US012741962B2

(12) United States Patent
Sintim et al.

(10) Patent No.: US 12,741,962 B2
(45) Date of Patent: Sep. 22, 2026

(54) 2,3-DISUBSTITUTED PYRIDO[3,4-B]PYRAZINE-CONTAINING COMPOUNDS AS KINASE INHIBITORS

(71) Applicant: Purdue Research Foundation, West Lafayette, IN (US)

(72) Inventors: Herman O. Sintim, Westfield, IN (US); Elizabeth Anne Larocque, Lowell, MA (US); Delmis E. Hernandez, Lafayette, IN (US); Neetu Dayal, Agra (IN)

(73) Assignee: Purdue Research Foundation, West Lafayette, IN (US)

( * ) Notice: Subject to any disclaimer, the term of this patent is extended or adjusted under 35 U.S.C. 154(b) by 594 days.

(21) Appl. No.: 18/009,311

(22) PCT Filed: Jun. 24, 2021

(86) PCT No.: PCT/US2021/038791

§ 371 (c)(1),
(2) Date: Dec. 8, 2022

(87) PCT Pub. No.: WO2021/262915

PCT Pub. Date: Dec. 30, 2021

(65) Prior Publication Data

US 2023/0219934 A1 Jul. 13, 2023

Related U.S. Application Data

(60) Provisional application No. 63/043,246, filed on Jun. 24, 2020.

(51) Int. Cl.

| | |
|---|---|
| ***C07D 471/04*** | (2006.01) |
| ***A61P 35/00*** | (2006.01) |
| ***C07D 403/14*** | (2006.01) |
| *A61K 31/4985* | (2006.01) |
| *A61P 1/14* | (2006.01) |
| *A61P 25/00* | (2006.01) |

(52) U.S. Cl.
CPC ............ *C07D 403/14* (2013.01); *A61P 35/00* (2018.01)

(58) Field of Classification Search
CPC ..... C07D 471/04; A61K 31/4985; A61P 1/14; A61P 25/00
See application file for complete search history.

(56) References Cited

U.S. PATENT DOCUMENTS

| | | | |
|---|---|---|---|
| 2007/0191376 | A1 | 8/2007 | Zou et al. |
| 2019/0177278 | A1 | 6/2019 | Sintim |

FOREIGN PATENT DOCUMENTS

| | | | |
|---|---|---|---|
| WO | 2009077766 | A1 | 6/2019 |
| WO | 2020053812 | A1 | 3/2020 |

OTHER PUBLICATIONS

International Search Report and Written Opinion, issued by the ISA/US, Commissioner for Patents, for International Application No. PCT/US2021/03791, Sep. 30, 2021.

*Primary Examiner* — Bruck Kifle

(74) *Attorney, Agent, or Firm* — Purdue Research Foundation

(57) ABSTRACT

The present invention generally relates to 2,3-Disubstituted pyrido[3,4-b]pyrazine-containing compounds as a kinase inhibitor and methods of uses thereof. Pharmaceutical compositions and methods for treating those kinase related diseases are within the scope of this invention.

1 Claim, 5 Drawing Sheets

(I) US20190177278A1

(II)

(III) HSL476

(IV)

(V) HSL212

(VI) HSL211

2,3-DISUBSTITUTED PYRIDO[3,4-B]PYRAZINE-CONTAINING COMPOUNDS AS KINASE INHIBITORS

CROSS-REFERENCE TO RELATED APPLICATIONS

The present U.S. patent application is a national stage entry under 35 U.S.C. § 371(b) of International Application No. PCT/US2021/038791, filed on Jun. 24, 2021, which relates to and claims the priority benefit of U.S. Provisional Application No. 63/043,246, filed Jun. 24, 2020, the content of which is hereby incorporated by reference in its entirety.

TECHNICAL FIELD

The present invention generally relates to 2,3-Disubstituted pyrido[3,4-b]pyrazine-containing compounds as kinase inhibitors and methods of uses thereof.

BACKGROUND

This section introduces aspects that may help facilitate a better understanding of the disclosure. Accordingly, these statements are to be read in this light and are not to be understood as admissions about what is or is not prior art.

Pancreatic cancer is one of the most lethal cancers with limited therapeutic options. The 5-year survival rate for localized pancreatic cancer is 37%. This drops to a miserly 3% for metastatic pancreatic cancer (*American Cancer Society. Cancer Facts* & *Figures* 2020. *Atlanta: American Cancer Society;* 2020*; https://www.cancer.org/content/dam/cancer-org/research/cancer-facts-and-statistics/annual-cancer-facts-and-figures/*2020*/cancer-facts-and-figures-*2020*.pdf*). Arguably pancreatic cancer has remained one of the few cancers that has resisted therapeutic breakthrough in the last decades, despite concerted efforts by many groups to develop therapeutics against this disease. HSL476 inhibits the growth of MiaPaCa-2 with IC50 of 25 nM. There are unmet medical needs.

BRIEF DESCRIPTION OF DRAWINGS

FIG. 2A: HSL476; FIG. 2B: HSL212; and FIG. 2C: HSL211.

DETAILED DESCRIPTION

Figure 1:
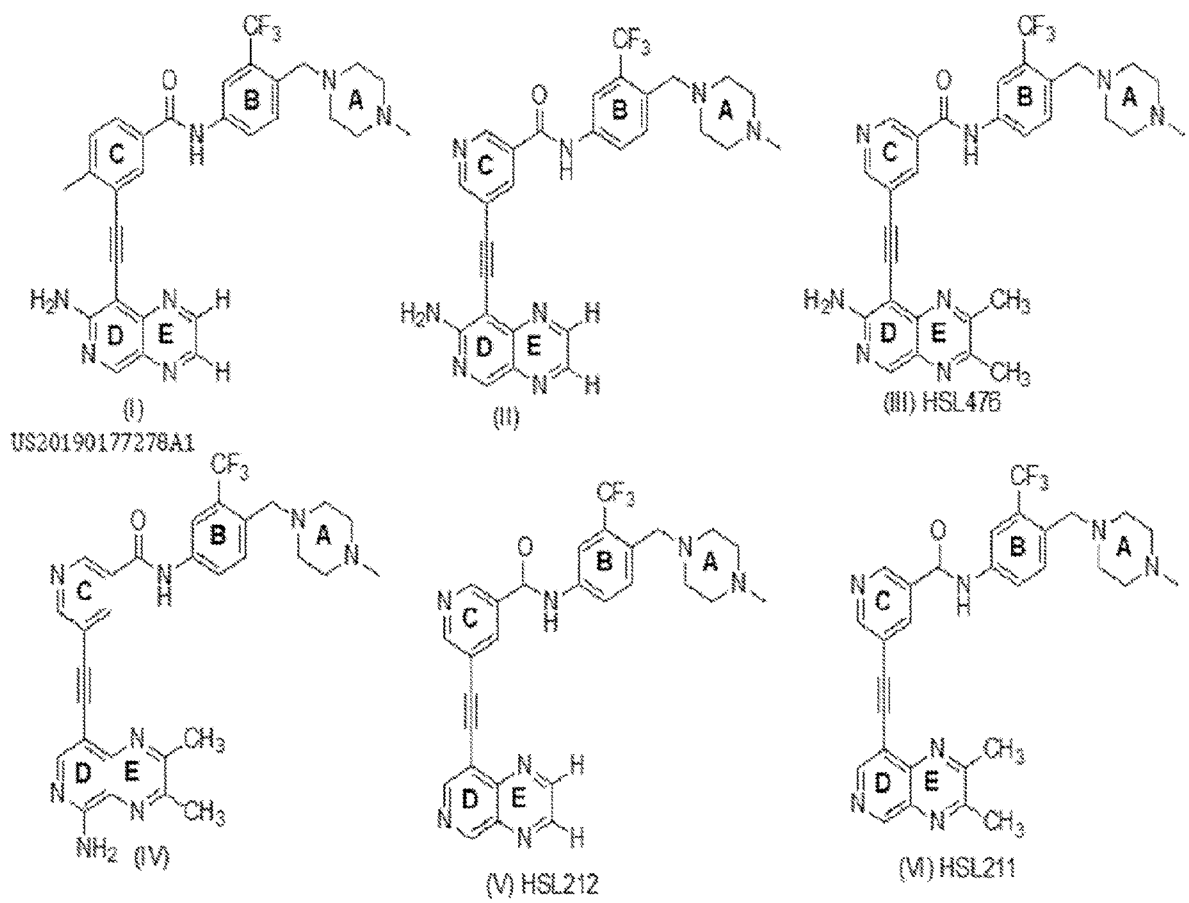
FIG. 1 depicts the structures of 2,3-disubstituted pyrido[3,4-b]pyrazine-containing compounds and unsubstituted analogs.

While the concepts of the present disclosure are illustrated and described in detail in the description herein, results in the description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═CHCH$_2$—, and the like. Examples of branched alkenyl groups include, but are not limited to, —CH═C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a mono alkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, $—CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other nontoxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

The present invention generally relates to compounds useful for the treatment of cancer. Pharmaceutical compositions and methods for treating those diseases are within the scope of this invention.

In some illustrative embodiments, the present invention relates to a method for treating a patient with a cancer comprising the step of administering a therapeutically effective amount of one or more compounds as disclosed herein, and one or more carriers, diluents, or excipients, to a patient in need of relief from kinase-related diseases.

In some illustrative embodiments, the present invention relates to a method for treating a patient with a cancer comprising the step of administering a therapeutically effective amount of one or more compounds as disclosed herein, in combination with one or more other compounds of the same or different mode of action, and one or more carriers, diluents, or excipients, to a patient in need of relief from kinase-related diseases.

In some illustrative embodiments, the present invention relates to a method for treating a patient with a cancer comprising the step of administering a therapeutically effective amount of one or more compounds as disclosed herein, and one or more carriers, diluents, or excipients, to a patient in need of relief from kinase-related diseases, wherein the conjugate confers cell-type or tissue type targeting or the conjugate targets another pathway that synergizes the action of compounds disclosed herein.

In some illustrative embodiments, the present invention relates to a method for treating a patient with a cancer comprising the step of administering a therapeutically effective amount of one or more compounds as disclosed herein, and one or more carriers, diluents, or excipients, to a patient in need of relief from kinase-related diseases, wherein the conjugate confers an improved aqueous solubility or a low clearance.

In some illustrative embodiments, the present invention relates to a pharmaceutical composition comprising one or more compounds as disclosed herein, together with one or more pharmaceutically acceptable diluents, excipients or carriers.

In some illustrative embodiments, the present invention relates to a pharmaceutical composition comprising one or more compounds as disclosed herein, together with one or more pharmaceutically acceptable diluents, excipients or carriers, wherein said pharmaceutical composition is for the treatment of kinase-related diseases.

In some illustrative embodiments, the present invention relates to the use of one or more compounds disclosed herein, together with one or more pharmaceutically acceptable diluents, excipients or carriers, in the manufacture of a medicament for the treatment of kinase-related diseases.

In some illustrative embodiments, the present invention relates to a pharmaceutical composition comprising nanoparticles of one or more compounds disclosed herein, together with one or more diluents, excipients or carriers.

In some illustrative embodiments, the present invention relates to a prodrug comprising one or more compounds as disclosed herein, wherein the prodrug moiety is removed at specific location, such as gastrointestinal or in blood or in tissues or in cancer specific.

In some illustrative embodiments, the present invention relates to an analog of compounds disclosed herein, wherein specific metabolic hot spots are modified with groups such as deuterium or fluorine.

In some other embodiments, the present invention relates to a method for treating a cancer comprising the step of administering a therapeutically effective amount of one or more compounds disclosed herein, and one or more carriers, diluents, or excipients, to a patient in need of relief from kinase-related diseases.

In some other embodiments, the present invention relates to a method for treating a cancer comprising the step of administering a therapeutically effective amount of a compound disclosed herein, in combination with one or more other compounds of the same or different mode of action, and one or more carriers, diluents, or excipients, to a patient in need of relief from kinase-related diseases.

In some illustrative embodiments, the present disclosure relates to . . . (will be filled in after the claims are finalized)

Figure 2A:
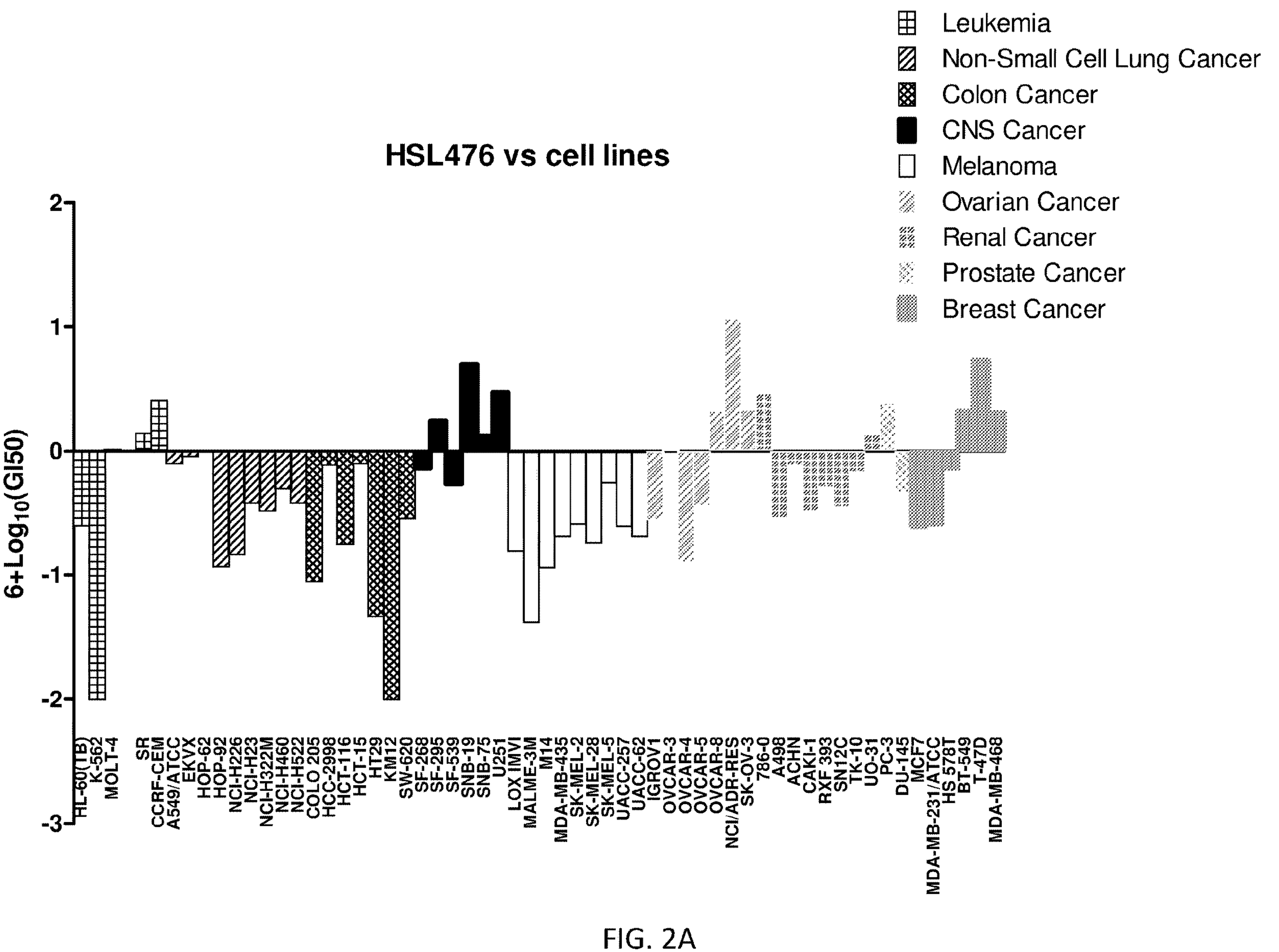
FIGS. 2A-2C show the anticancer activities of pyrido[3,4-b]pyrazine-containing compounds against NCI-60. Value at 0 represents GI50 of 1 μM.
Figure 2B:
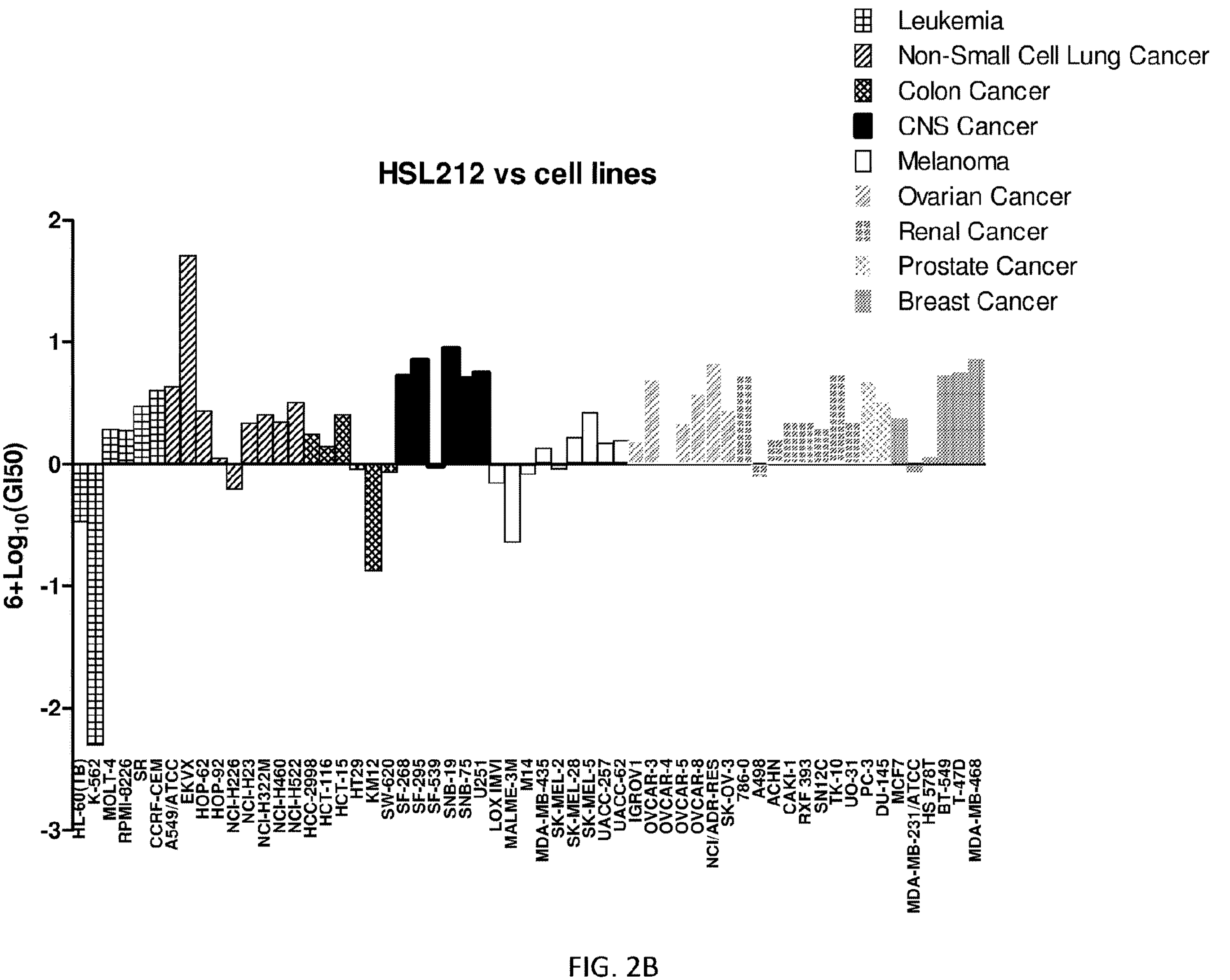
Figure 2C:
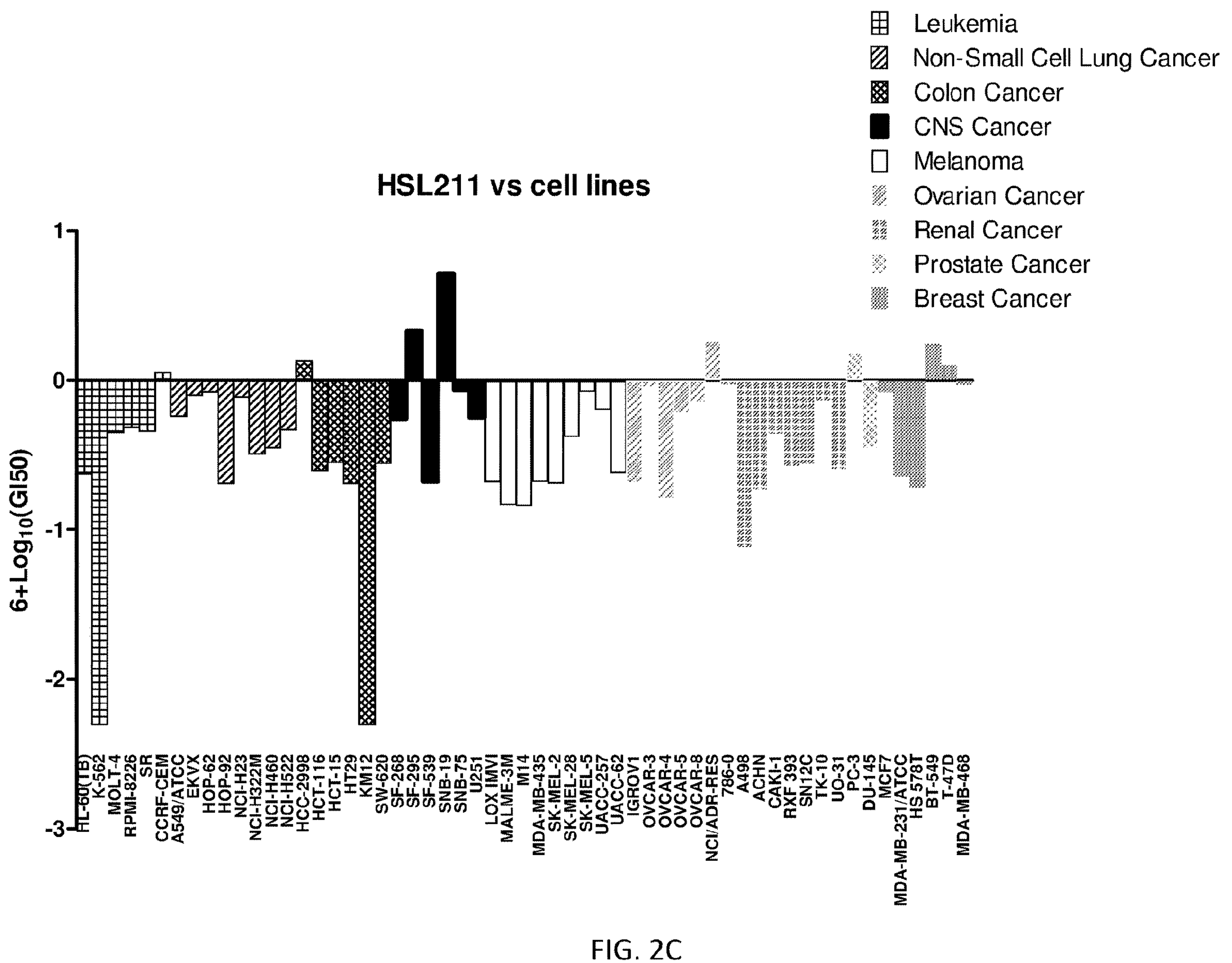
Figure 3:
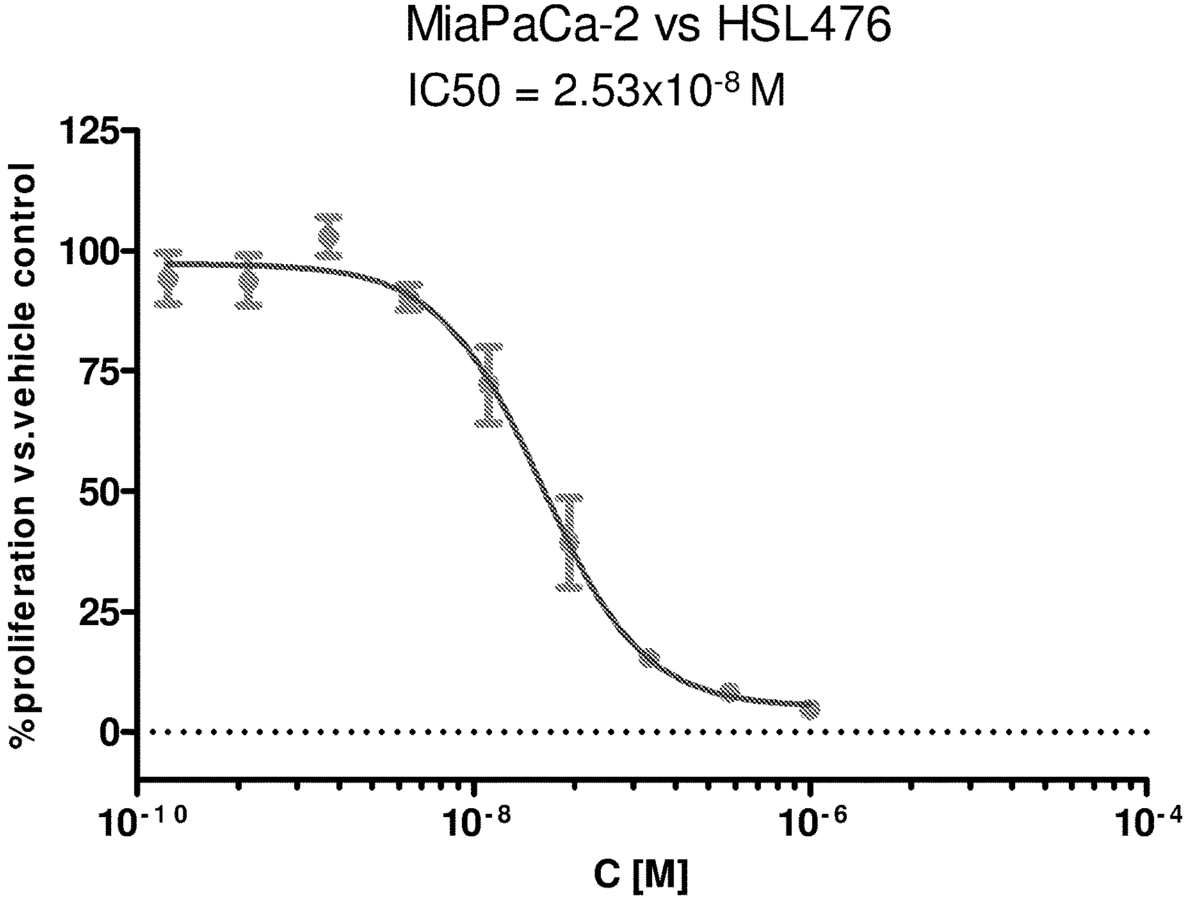
FIG. 3 demonstrates the potent inhibition of pancreatic cancer cell line, MiaPaCa-2, growth by HSL476. IC50=25 nM.

There are over 500 protein kinases in the human cell and many of such kinases have been targeted for therapeutic purposes. Sintim teaches us (US20190177278A1) that alkynyl pyrido[3,4-b]pyrazine compound (I), FIG. 1, is a kinase inhibitor with potent activity against acute myeloid leukemia and chronic myeloid leukemia due to inhibition of FLT3 and ABL1 kinases respectively. Sintim also teaches us (PCT/IB2019/057711) that changing a methyl benzamide moiety in (I), KR10-2008-0081191A and US2015-0105377, into nicotinamide moiety (E Larocque, et al., *ACS Omega* 2020, 5, 6, 2690-2698; E. Larocque, et al., ChemMedChem 2018, 13, 1172-1180; N Naganna, et al., EBioMedicine 2019, 40, 231-239) could reduce the inhibition of Src kinases, which could reduce cardiovascular toxicities (*ACS Omega* 2020, 5, 6, 2690). We have discovered (this disclosure) that further substituting the pyrido[3,4-b]pyrazine moiety with alkyl groups drastically improved the inhibition of solid tumors, such as non-small cell lung cancer (NSCLC) and colon cancer (FIG. 2). For example, HSL212 and HSL211 differ by the 2,3-dimethyl substitution and both compounds inhibit K562 cell line (leukemia) with $GI_{50}$ less than 5 nM (National Cancer Institute Developmental Therapeutics Program In-Vitro Testing Results: NSC: D-805100/1; Experiment ID: 1905RS90 versus NSC: D-805101/1; Experiment ID: 1808NS91). However, for many solid cancers, HSL211 is vastly different from HSL212. A case in point is that HSL211 inhibits some lung and colon cancers ~100× more potently than HSL212. *Specifically, HSH*211 *inhibits* EKVX (NSCLC) and KM12 (colon and driven by TrkA kinase) *with G*150 *of* 484 *nM and less than* 5 *nM respectively whereas HSL*212 *inhibits EKVX and KM*12 *with G*150>50 *μM and* 136 *nM respectively* (National Cancer Institute Developmental Therapeutics Program In-Vitro Testing Results: NSC: D-805100/1; Experiment ID: 1905RS90 versus NSC: D-805101/1; Experiment ID: 1808NS91).

Pancreatic cancer is one of the most lethal cancers with limited therapeutic options. The 5-year survival rate for localized pancreatic cancer is 37%. This drops to a miserly 3% for metastatic pancreatic cancer (*American Cancer Society. Cancer Facts* & *Figures* 2020. *Atlanta: American Cancer Society;* 2020; https://www.cancer.org/). Arguably pancreatic cancer has remained one of the few cancers that has resisted therapeutic breakthrough in the last decades, despite concerted efforts by many groups to develop therapeutics against this disease. HSL476 inhibits the growth of MiaPaCa-2 with IC50 of 25 nM.

Activity Against RET-Driven Cancers:

Selpercatinib and pralsetinib are approved by the FDA for the treatment of RET-driven cancers. Recent studies have found several mutations in RET kinase (such as RETG810R/C/S/V) that cause resistance to selpercatinib and pralsetinib (*Ann. Oncol.* 2021, 32, 261-268 and *J. Thorac. Oncol.* 2020, 15, 541-549). Also MET or KRAS amplification and other non-RET mutations conferred resistance to selpercatinib and pralsetinib (Clin Cancer Res 2021, 27, 34-42 and Annals of Oncology, 2020, 31(12), 1725-1733). HSL476 inhibited Selpercatinib and pralsetinib-resistant cell lines harboring RET solvent front mutations with IC50 values less than 20 nM. For example, HSL476 inhibited cell line harboring RET G810R with IC50 of 18 nM while under similar conditions the IC50 for ponatinib was 77 nM, Selpercatinib was 2623 nM and pralsetinib was 7323 nM. HSL476 is orally bioavailable, well tolerated in mice and at 25 mg/Kg (daily), HSL476 could reduce growth tumor harboring solvent front RET810 mutation whereas selpercatinib was ineffective.

The aforementioned examples clearly demonstrates that the substitution of alkynyl pyrido[3,4-b]pyrazine compound (I), revealed in US20190177278A1, with alkyl groups at the 2,3-positions and the replacement of the benzamide core (ring C) with nicotinamide affords compounds with potent activities against solid tumors. Substitution with the more bulky ethyl group led to compounds that are more active than the unsubstituted versions but less potent than the methyl substituted compounds. Enhancement of drug potencies via methyl substitution termed the "magic methyl" has been documented in the literature (J. Zhao, et al., *J. Med. Chem.* 2018, 61, 22, 10242-10254; A Lodola, et al., *J. Med. Chem.* 2017, 60, 10, 4304-4315). However, it is not always obvious which position in a molecule is amenable to methylation and hence the identification of such sites requires the synthesis of a vast library of analogs, which prior reports do not teach how to arrive at such analogs. Secondly, although the substitution with methyl groups can lead to activity enhancement, Jorgensen found (after evaluating over 2000 cases) that a 100-fold enhancement of activity upon methylation occurs in about 0.5% of the cases (C S Leung, et al., J. Med. Chem., 2012, 55, 9, 4489-4500). In some cases, the introduction of a methyl group actually hurts activity, thus the so-called "magic methyl" is not a certainty.

EXPERIMENTAL

Cell Culture: MIA PaCa-2 cells were cultured in RPMI media supplemented with 10% fetal bovine serum, 1% GlutaMax Supplement (GIBCO™), 1% Penicillin-Streptomycin (GIBCO™). Cells were seeded in a 96-well plate at $1.1\times10^4$ cells/mL. Cells were incubated at 20° C. for 24 hours after which plates were treated in triplicates with 10 uL of compound (0.6 μM in DMSO) that was further diluted in the same media (5 μL of compound into 145 μL of media). For $IC_{50}$ compounds were tested at 9 different concentrations, initial concentration of 0.6 μM in DMSO and subsequently diluted by a third for the other 8 concentrations. This was incubated at 20° C. for 72 hours after which 10 uL of The CellTitre Blue Cell Viability Assay (Promega, Madison WI) was added to each well and incubated at 20° C. for 3 hours. Plates were read on a CYTATION™ 5 Cell Imaging Multi-Mode Reader (BioTek). Appropriate controls were used. Graphed using GraphPadPrism 5.0 Software.

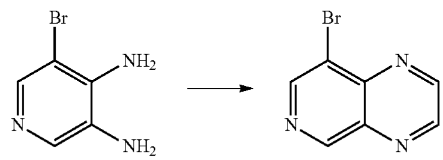 [SMILES: Nc1cncc(Br)c1N ; Brc1cncc2nccnc12]

HSL215: 8-bromopyrido[3,4-b]pyrazine

To a reaction vial, 5-bromopyridine-3,4-diamine (250 mg, 1.33 mmol, 1 equiv.) and ethanol (10 mL) were added. Oxalaldehyde (77 mg, 1.33 mmol, 1 equiv.) was then added. The reaction was then allowed to stir at room temperature for 6 hours. Upon reaction completion, crude mixture was concentrated under reduced pressure. Pure compound was obtained via column chromatography (10% MeOH/$CH_2Cl_2$). Yield=85% TLC Rf=0.76 (10% MeOH/$CH_2Cl_2$) $^1H$ NMR (500 MHz, DMSO-d6) δ 9.48 (s, 1H), 9.27 (d, J=1.8 Hz, 1H), 9.17 (d, J=1.7 Hz, 1H), 9.12 (s, 1H). $^{13}C$ NMR (126 MHz, DMSO) δ 154.2, 151.6, 149.1, 148.9, 143.0, 138.9, 120.2.

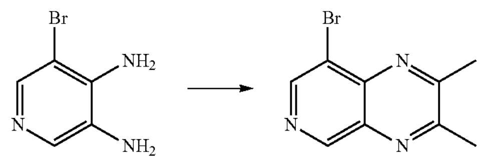

HSL176: 8-bromo-2,3-dimethylpyrido[3,4-b]pyrazine

To a reaction vial, 5-bromopyridine-3,4-diamine (100 mg, 0.532 mmol, 1 equiv.) and ethanol (10 mL) were added. Biacetyl (45.8 mg, 0.532 mmol, 1 equiv.) was then added. The reaction was then allowed to stir at room temperature for 2 hours. Upon reaction completion, crude mixture was concentrated under reduced pressure. Pure compound was obtained via column chromatography (10% MeOH/$CH_2Cl_2$). Yield=quantitative TLC Rf=0.4 ($CH_2Cl_2$) $^1H$ NMR (500 MHz, DMSO-$d_6$) δ 9.21 (s, 1H), 8.90 (s, 1H), 2.73 (s, 3H), 2.71 (s, 3H). $^{13}C$ NMR (126 MHz, DMSO) δ 161.3, 158.3, 152.4, 147.8, 141.4, 137.2, 119.3, 23.9, 23.2.

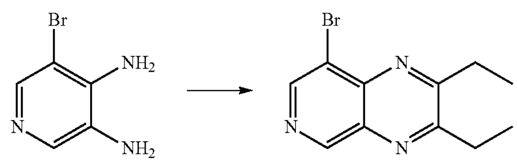

HSL452: 8-bromo-2,3-diethylpyrido[3,4-b]pyrazine

To a reaction vial, 5-bromopyridine-3,4-diamine (100 mg, 0.531 mmol, 1 equiv.) and MeOH (10 mL) were added. Hexane-3,4-dione (60.6 mg, 0.531 mmol, 1 equiv.) was then added. The reaction was then allowed to stir at room temperature for 2.5 hours. Upon reaction completion, crude mixture was concentrated under reduced pressure. Pure compound was obtained via column chromatography (10%

$MeOH/CH_2Cl_2$). Yield=61% TLC Rf=0.8 (10% $MeOH/CH_2Cl_2$)$^1$H NMR (500 MHz, DMSO-$d_6$) δ 9.30 (s, 1H), 8.96 (s, 1H), 3.11 (dq, J=11.1, 7.3 Hz, 4H), 1.36 (dt, J=11.0, 7.3 Hz, 6H).

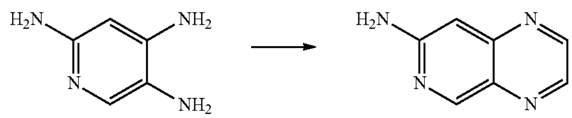

HSL404: pyrido[3,4-b]pyrazin-7-amine

To a reaction vial, pyridine-2,4,5-triamine (80 mg, 0.645 mmol, 1 equiv.) and ethanol (5 mL) were added. Oxalaldehyde (37.41 mg, 0.645 mmol, 1 equiv.) was then added. The reaction was then allowed to stir at room temperature for 6 hours. Upon reaction completion, crude mixture was concentrated under reduced pressure. Pure compound was obtained via column chromatography (DMC). Yield=60% TLC Rf=0.3 (10% $MeOH/CH_2Cl_2$) $^1$H NMR (500 MHz, DMSO-$d_6$) δ 8.94 (d, J=0.8 Hz, 1H), 8.75 (d, J=1.8 Hz, 1H), 8.49 (d, J=1.8 Hz, 1H), 6.69 (d, J=0.8 Hz, 1H), 6.58 (s, 2H). $^{13}$C NMR (126 MHz, DMSO) δ 160.1, 154.0, 150.5, 147.7, 142.1, 132.3, 97.3.

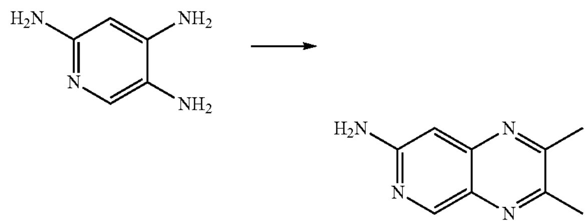

HSL405: 2,3-dimethylpyrido[3,4-b]pyrazin-7-amine

To a reaction vial, pyridine-2,4,5-triamine (80 mg, 0.645 mmol, 1 equiv.) and ethanol (5 mL) were added. Biacetyl (55.54 mg, 0.645 mmol, 1 equiv.) was then added. The reaction was then allowed to stir at room temperature for 2 hours. Upon reaction completion, crude mixture was concentrated under reduced pressure. Pure compound was obtained via column chromatography (DCM). Yield=89% TLC Rf=0.45 (10% $MeOH/CH_2Cl_2$). $^1$H NMR (500 MHz, DMSO-$d_6$) δ 8.75 (s, 1H), 6.60 (d, J=0.8 Hz, 1H), 6.28 (s, 2H), 2.56 (s, 3H), 2.53 (s, 3H). $^{13}$C NMR (126 MHz, DMSO) δ 159.4, 159.2, 151.9, 150.3, 146.2, 130.6, 97.5, 23.7, 22.8.

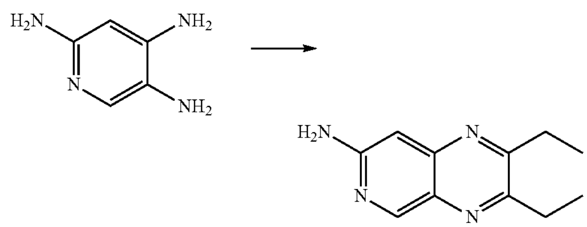

HSL498: 2,3-diethylpyrido[3,4-b]pyrazin-7-amine

To a reaction vial, pyridine-2,4,5-triamine (150 mg, 0.797 mmol, 1 equiv.) and ethanol (10 mL) were added. Hexane-3,4-dione (90 mg, 0.645 mmol, 1 equiv.) was then added. The reaction was then allowed to stir for 2.5 hours at room temperature. An additional equivalent of hexane-3,4-dione was added 2.5 hours later. The reaction was then allowed to stir for an additional 1.5 hours. Upon reaction completion, crude mixture was concentrated under reduced pressure. Pure compound was obtained via column chromatography (DCM). Yield=80% TLC Rf=0.8 (10% $MeOH/CH_2Cl_2$). $^1$H NMR (500 MHz, DMSO-$d_6$) δ 8.78 (d, J=0.8 Hz, 1H), 6.63 (d, J=0.8 Hz, 1H), 6.27 (s, 2H), 2.89 (dq, J=14.7, 7.4 Hz, 4H), 1.25 (td, J=7.4, 0.9 Hz, 6H). $^{13}$C NMR (126 MHz, DMSO) δ 162.2, 159.5, 153.6, 152.1, 145.9, 130.4, 97.7, 39.3, 39.1, 28.1, 27.3, 12.0, 11.7.

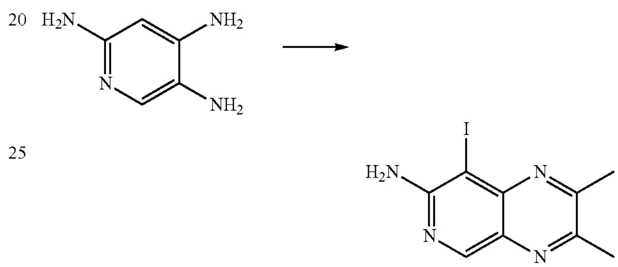

HSL415: 8-iodo-2,3-dimethylpyrido[3,4-b]pyrazin-7-amine 2,3-dimethylpyrido[3,4-b]pyrazin-7-amine (94.1 mg, 0.540 mmol, 1 equiv) were added to a reaction vial with methanol (10 mL). The reaction was then cooled to 0° C. and NIS (133.8 mg, 0.594 mol, 1.1 equiv) was slowly added over 10 minutes. The reaction was then allowed to run at 0° C. for 15 minutes. Crude mixed was concentrated down under reduced pressure. Pure product was obtained via column chromatography (1:1 EA/HEX). Yield=90.2% TLC Rf=0.9 (10% $MeOH/CH_2Cl_2$). $^1$H NMR (500 MHz, DMSO-$d_6$) δ 8.71 (s, 1H), 2.64 (s, 3H), 2.58 (s, 3H).

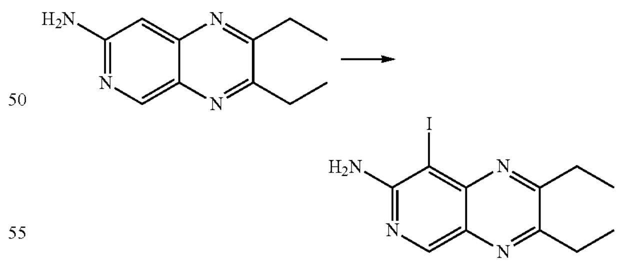

HSL501: 2,3-diethyl-8-iodopyrido[3,4-b]pyrazin-7-amine 2,3-diethylpyrido[3,4-b]pyrazin-7-amine (100 mg, 0.500 mmol, 1 equiv) were added to a reaction vial with methanol (5 mL). The reaction was then cooled to 0° C. and NIS (112 mg, 1.1 equiv) was slowly added over 10 minutes. The reaction was then allowed to run at 0° C. for 10 minutes. Crude mixed was concentrated down under reduced pressure. Pure product was obtained via column chromatography (1:1 EA/HEX). Yield=64% TLC Rf=0.6 (1:1 EA/HEX). $^{1}$H NMR (500 MHz, DMSO-$d_6$) δ 8.73 (s, 1H), 6.49 (s, 2H), 2.99 (q, J=7.3 Hz, 2H), 2.93 (q, J=7.4 Hz, 2H), 1.34 (t, J=7.2 Hz, 3H), 1.28 (t, J=7.4 Hz, 3H). $^{13}$C NMR (126 MHz, DMSO) δ 163.0, 159.1, 154.7, 151.8, 145.4, 131.1, 74.4, 27.9, 26.9, 11.9, 11.3.

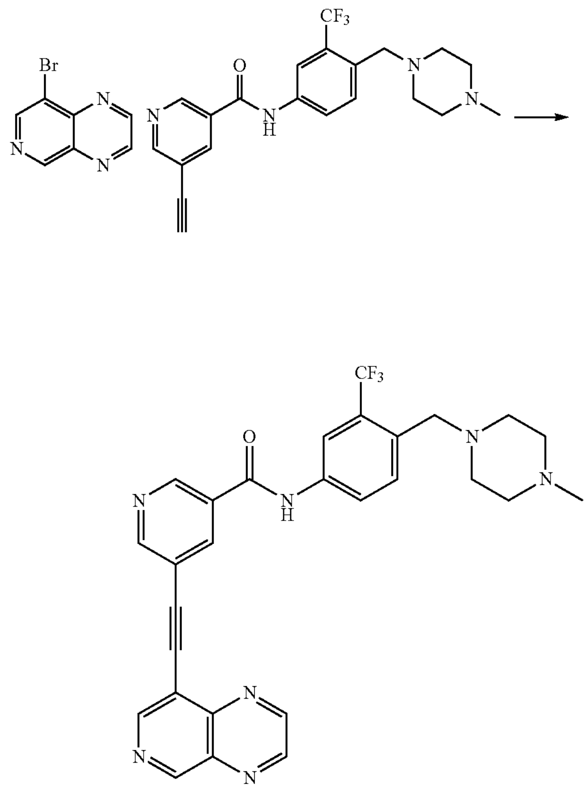

HSL212:N-(4-((4-methylpiperazin-1-yl)methyl)-3-(trifluoromethyl)phenyl) (pyrido[3,4-b]pyrazin-8-ylethynyl)nicotinamide A solution of 8-bromopyrido[3,4-b]pyrazine (100 mg, 0.476 mmol, 1 equiv), $Pd(PPh_3)_2Cl_2$ (10 mol %), CuI (5 mol %) and Triphenylphosphine (10 mg) in Triethylamine (1 mL) was de-oxygenated using argon gas for 10 minutes. A de-oxygenated solution of alkyne (101 mg, 0.252 mmol, 0.53 equiv) in DMF (4 mL) was added slowly over a period of 10 min to the TEA solution. The reaction temperature was increased to 55° C. and allowed to stir for 7 hours. The crude compound was extracted using EtOAc (3×40 mL) and washed with brine (1×100 mL). Combined organic layers were dried over anhydrous sodium sulphate, filtered and concentrated under reduced pressure. The pure product obtained via flash column chromatography (10% MeOH/$CH_2Cl_2$). Yield=16.49% TLC Rf=0.2 (10% MeOH+1% $NH_4OH/CH_2Cl_2$). $^{1}$H NMR (500 MHz, DMSO-$d_6$) δ 10.80 (s, 1H), 9.55 (s, 1H), 9.30 (d, J=1.7 Hz, 1H), 9.20 (d, J=1.7 Hz, 1H), 9.16 (s, 1H), 9.14 (d, J=2.0 Hz, 1H), 9.04 (s, 1H), 8.61 (t, J=2.1 Hz, 1H), 8.19 (d, J=2.0 Hz, 1H), 8.04 (dd, J=8.5, 1.7 Hz, 1H), 7.72 (d, J=8.5 Hz, 1H), 3.56 (s, 2H), 2.39 (s, 8H), 2.17 (s, 3H).

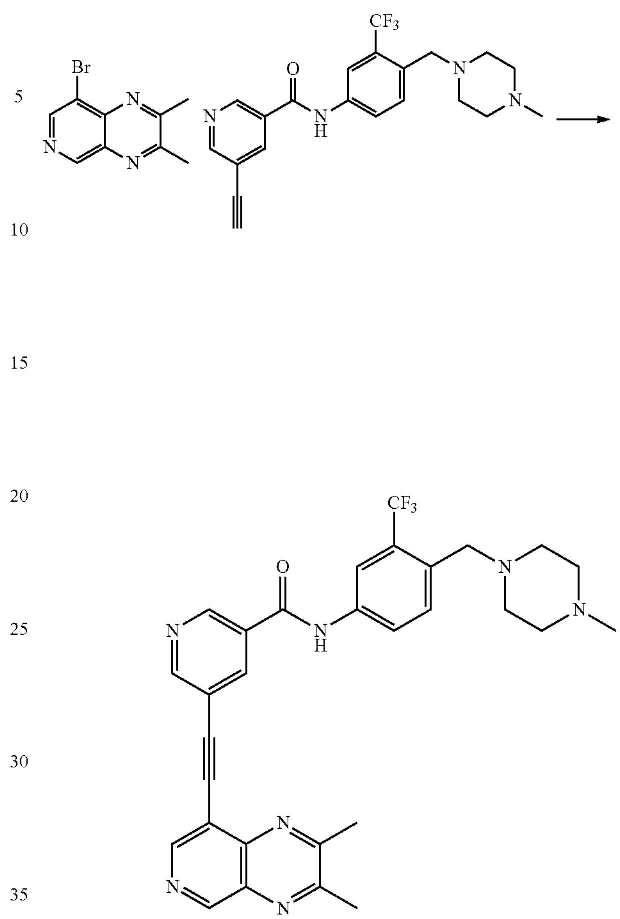

HSL211:5-((2,3-dimethylpyrido[3,4-b]pyrazin-8-yl) ethynyl)-N-(4-((4-methylpiperazin-1-yl)methyl)-3-(trifluoromethyl)phenyl)nicotinamide A solution of 8-bromo-2,3-dimethylpyrido[3,4-b]pyrazine (100 mg, 0.420 mmol, 1 equiv), $Pd(PPh_3)_2Cl_2$ (10 mol %), CuI (5 mol %) and Triphenylphosphine (10 mg) in Triethylamine (1 mL) was de-oxygenated using argon gas for 10 minutes. A de-oxygenated solution of alkyne (115 mg, 0.286 mmol, 0.68 equiv) in DMF (4 mL) was added slowly over a period of 10 min to the TEA solution. The reaction temperature was increased to 55° C. and allowed to stir for 7 hours. The crude compound was extracted using EtOAc (3×40 mL) and washed with brine (1×100 mL). Combined organic layers were dried over anhydrous sodium sulphate, filtered and concentrated under reduced pressure. The pure product obtained via flash column chromatography (10% MeOH/$CH_2Cl_2$). Yield=22.4% TLC Rf=0.2 (10% MeOH+1% $NH_4OH/CH_2Cl_2$). $^{1}$H NMR (500 MHz, DMSO-$d_6$) δ 10.80 (s, 1H), 9.37 (s, 1H), 9.13 (s, 1H), 9.02 (d, J=7.8 Hz, 2H), 8.59 (t, J=2.0 Hz, 1H), 8.20 (d, J=1.9 Hz, 1H), 8.07-8.00 (m, 1H), 7.72 (d, J=8.5 Hz, 1H), 3.56 (s, 2H), 2.80 (s, 3H), 2.75 (s, 3H), 2.38 (s, 8H), 2.16 (s, 3H). $^{13}$C NMR (126 MHz, DMSO) δ 163.8, 161.1, 158.1, 154.6, 153.6, 150.2, 149.1, 143.5, 138.3, 138.0, 135.8, 133.0, 131.8, 130.4, 124.0, 119.3, 117.7, 116.1, 93.2, 88.3, 57.9, 55.1, 53.1, 46.1, 40.5, 24.2, 23.5.

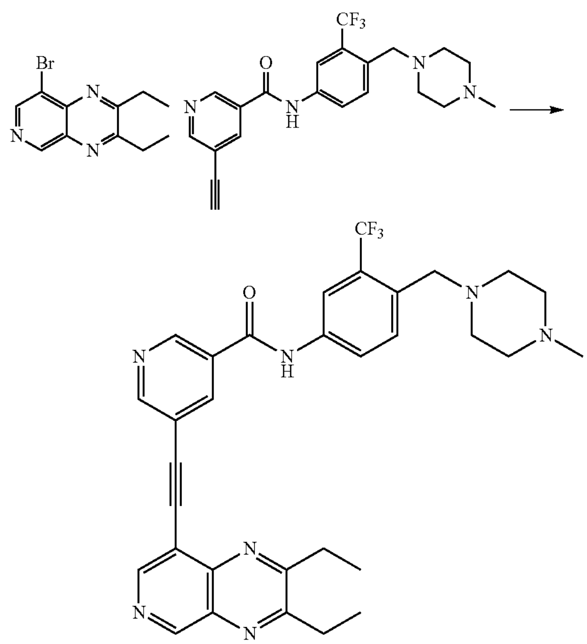

HSL517:5-((2,3-diethylpyrido[3,4-b]pyrazin-8-yl) ethynyl)-N-(4-((4-methylpiperazin-1-yl)methyl)-3-(trifluoromethyl)phenyl)nicotinamide A solution of 8-bromo-2,3-diethylpyrido[3,4-b]pyrazine (104 mg, 0.393 mmol, 1 equiv), $Pd(PPh_3)_2Cl_2$ (10 mol %), CuI (5 mol %) and Triphenylphosphine (10 mg) in Triethylamine (1.5 mL) was de-oxygenated using argon gas for 10 minutes. A de-oxygenated solution of alkyne (190 mg, 0.476 mmol, 1.2 equiv) in DMF (4 mL) was added slowly over a period of 10 min to the TEA solution. The reaction temperature was increased to 55° C. and allowed to stir overnight. The crude compound was concentrated under reduced pressure. The pure product obtained via flash column chromatography (10% $MeOH/CH_2Cl_2$). Yield=52% TLC Rf=0.3 (10% $MeOH/CH_2Cl_2$). $^1H$ NMR (500 MHz, DMSO-$d_6$) δ 10.80 (s, 1H), 9.38 (s, 1H), 9.13 (d, J=2.2 Hz, 1H), 9.00 (d, J=2.0 Hz, 2H), 8.55 (t, J=2.1 Hz, 1H), 8.20 (d, J=2.2 Hz, 1H), 8.04 (dd, J=8.5, 2.2 Hz, 1H), 7.72 (d, J=8.5 Hz, 1H), 3.59 (s, 2H), 3.15 (q, J=7.3 Hz, 2H), 3.10 (q, J=7.3 Hz, 2H), 2.62 (s, 8H), 2.37 (s, 3H), 1.42 (t, J=7.2 Hz, 3H), 1.36 (t, J=7.3 Hz, 3H).

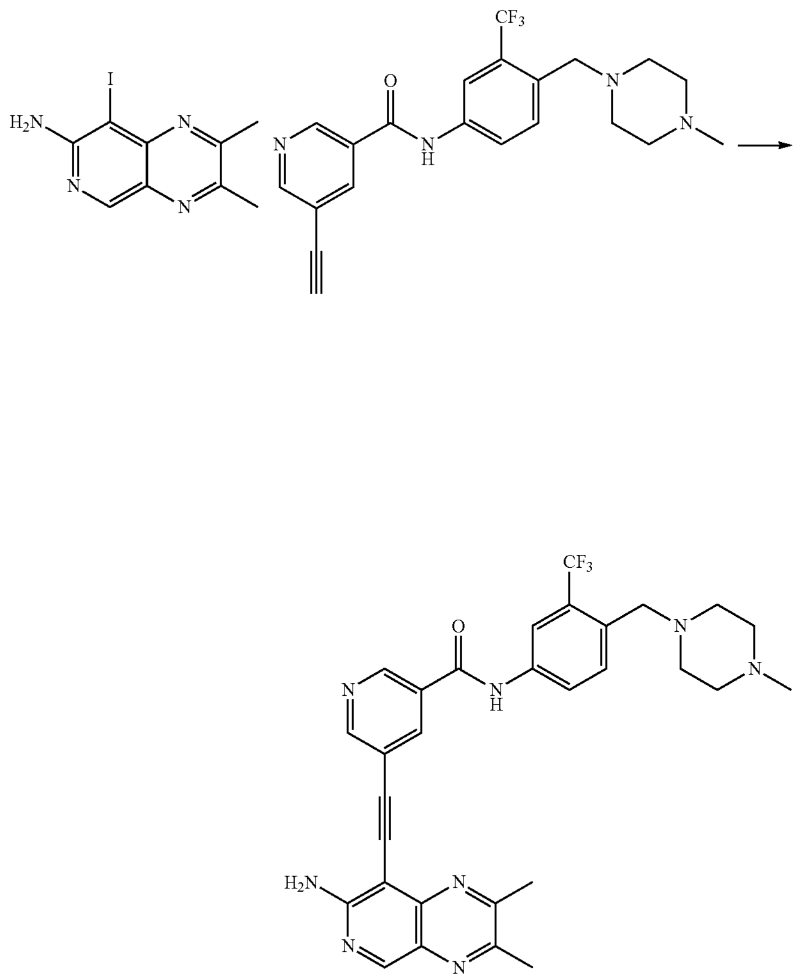

HSL476:5-((7-amino-2,3-dimethylpyrido[3,4-b]pyrazin-8-yl)ethynyl)-N-(4-((4-methylpiperazin-1-yl)methyl)-3-(trifluoromethyl)phenyl)nicotinamide A solution of 8-iodo-2,3-dimethylpyrido[3,4-b]pyrazin-7-amine (78.1 mg, 0.261 mmol, 1 equiv), $Pd(PPh_3)_2Cl_2$ (10 mol %), CuI (5 mol %) and Triphenylphosphine (10 mg) in Triethylamine (1.5 mL) was de-oxygenated using argon gas for 10 minutes. A de-oxygenated solution of alkyne (126 mg, 0.313 mmol, 1.2 equiv) in DMF (4 mL) was added slowly over a period of 10 min to the TEA solution. The reaction temperature was increased to 55° C. and allowed to stir overnight. The crude compound concentrated under reduced pressure. The pure product obtained via flash column chromatography (10% $MeOH/CH_2Cl_2$). Yield=40.7% TLC Rf=0.12 (10% $MeOH/CH_2Cl_2$). $^1H$ NMR (500 MHz, DMSO-$d_6$) δ 10.84 (s, 1H), 9.06 (s, 2H), 8.86 (s, 1H), 8.62 (s, 1H), 8.22 (s, 1H), 8.05 (d, J=8.6 Hz, 1H), 7.72 (d, J=8.5 Hz, 1H), 7.04 (s, 2H), 3.57 (s, 2H), 2.67 (s, 3H), 2.58 (s, 3H), 2.42 (s, 8H), 2.21 (s, 3H). $^{13}C$ NMR (126 MHz, DMSO) δ 164.2, 160.4, 159.9, 154.5, 153.3, 151.1, 147.9, 146.0, 138.4, 137.7, 132.8, 131.8, 130.3, 128.1, 125.8, 124.0, 120.6, 117.8, 117.7, 95.3, 90.4, 88.5, 57.8, 54.9, 52.7, 45.7, 40.5, 24.0, 22.7.

HSL507: 5-((7-amino-2,3-diethylpyrido[3,4-b]pyrazin-8-yl)ethynyl)-N-(4-((4-methylpiperazin-1-yl)methyl)-3-(trifluoromethyl)phenyl)nicotinamide A solution of 8-iodo-2,3-diethylpyrido[3,4-b]pyrazin-7-amine (80 mg, 0.243 mmol, 1 equiv), $Pd(PPh_3)_2Cl_2$ (10 mol %), CuI (5 mol %) and Triphenylphosphine (10 mg) in Triethylamine (1.5 mL) was de-oxygenated using argon gas for 10 minutes. A de-oxygenated solution of alkyne (117 mg, 0.292 mmol, 1.2 equiv) in DMF (4 mL) was added slowly over a period of 10 min to the TEA solution. The reaction temperature was increased to 55° C. and allowed to stir overnight. The crude compound concentrated under reduced pressure. The pure product obtained via flash column chromatography (10% $MeOH/CH_2Cl_2$). Yield=63.1% TLC Rf=0.13 (10% $MeOH/CH_2Cl_2$). $^1H$ NMR (500 MHz, DMSO-$d_6$) δ 10.84 (s, 1H), 9.05 (d, J=2.2 Hz, 1H), 9.00 (d, J=2.0 Hz, 1H), 8.88 (s, 1H), 8.58 (t, J=2.1 Hz, 1H), 8.20 (d, J=2.2 Hz, 1H), 8.04 (dd, J=8.6, 2.2 Hz, 1H), 7.72 (d, J=8.5 Hz, 1H), 7.04 (s, 2H), 3.58 (s, 2H), 3.02 (q, J=7.3 Hz, 2H), 2.94 (q, J=7.4 Hz, 2H), 2.54 (s, 8H), 2.31 (s, 3H), 1.38 (t, J=7.3 Hz, 3H), 1.29 (t, J=7.4 Hz, 3H). $^{13}C$ NMR (126 MHz, DMSO) δ 164.3, 162.6, 160.3, 154.4, 154.2, 153.4, 147.7,

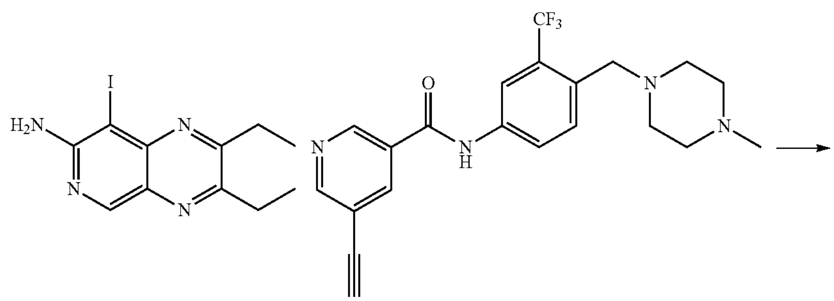

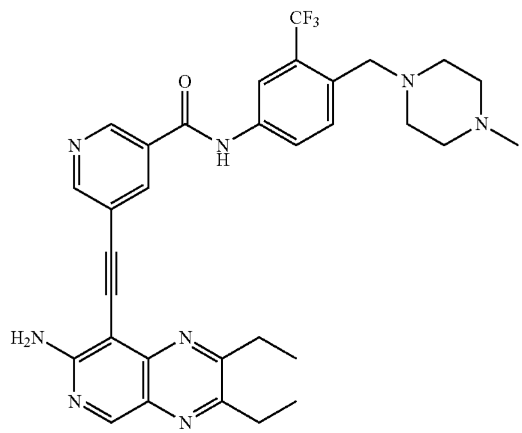

145.8, 138.4, 137.7, 132.7, 131.9, 130.4, 130.1, 127.9, 125.8, 124.0, 120.8, 117.7, 95.4, 90.6, 88.6, 57.7, 54.6, 52.2, 45.2, 28.2, 27.2, 11.9, 11.3.

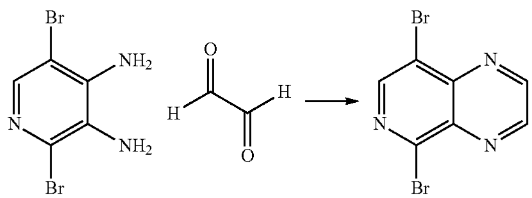

HSL521: 5,8-dibromopyrido[3,4-b]pyrazine

To a reaction vial, 2,5-dibromopyridine-3,4-diamine (300 mg, 0.123 mmol, 1 equiv.) and ethanol (10 mL) were added. Oxalaldehyde (130 mg, 2.25 mmol, 2 equiv.) was then added. The reaction was then allowed to stir at room temperature for 4 hours. After 4 hours 2 more equivalents of oxalaldehyde was added. The reaction was then allowed to stir for 3 days. Upon reaction completion, crude mixture was concentrated under reduced pressure. Pure compound was obtained via column chromatography (1:1 EA/Hex). Yield=31% TLC Rf=0.2 (100% Hexanes). $^1$H NMR (500 MHz, DMSO-$d_6$) δ 9.32 (d, J=1.8 Hz, 1H), 9.23 (d, J=1.8 Hz, 1H), 8.93 (s, 1H). $^{13}$C NMR (126 MHz, DMSO) δ 152.1, 149.7, 147.7, 146.7, 144.5, 137.8, 120.8.

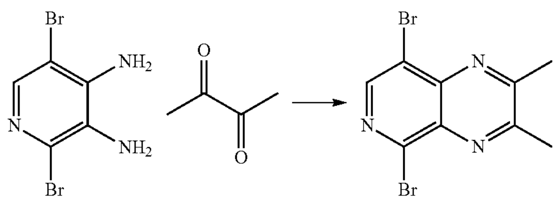

HSL522: 5,8-dibromo-2,3-dimethylpyrido[3,4-b]pyrazine

To a reaction vial, 2,5-dibromopyridine-3,4-diamine (300 mg, 0.123 mmol, 1 equiv.) and ethanol (10 mL) were added. Biacetyl (130 mg, 2.25 mmol, 2 equiv.) was then added. The reaction was then allowed to stir at room temperature for 4 hours. After 4 hours 2 more equivalents of biacetyl was added. The reaction was then allowed to stir for 3 days. Upon reaction completion, crude mixture was concentrated under reduced pressure. Pure compound was obtained via column chromatography (1:1 EA/Hex). Yield=82% TLC Rf=0.7 (1:1 EA/Hex) $^1$H NMR (500 MHz, DMSO-$d_6$) δ 8.78 (s, 1H), 2.79 (s, 3H), 2.77 (s, 3H). $^{13}$C NMR (126 MHz, DMSO) δ 162.0, 159.3, 146.8, 145.1, 142.7, 135.9, 119.9, 23.7, 23.5.

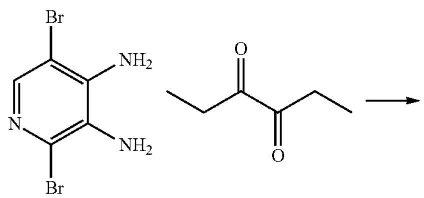

-continued

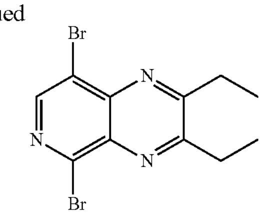

HSL523: 5,8-dibromo-2,3-diethylpyrido[3,4-b]pyrazine

To a reaction vial, 2,5-dibromopyridine-3,4-diamine (300 mg, 0.123 mmol, 1 equiv.) and ethanol (10 mL) were added. Hexane-3,4-dione (256 mg, 2.25 mmol, 2 equiv.) was then added. The reaction was then allowed to stir at room temperature for 4 hours. After 4 hours, 2 more equivalents of hexane-3,4-dione was added. The reaction was then allowed to stir for 3 days. Upon reaction completion, crude mixture was concentrated under reduced pressure. Pure compound was obtained via column chromatography (1:1 EA/Hex). Yield=82% TLC Rf=0.85 (1:1 EA/Hex) $^1$H NMR (500 MHz, DMSO-$d_6$) δ 8.79 (s, 1H), 3.13 (p, J=7.4 Hz, 4H), 1.37 (td, J=7.2, 2.7 Hz, 6H). $^{13}$C NMR (126 MHz, DMSO) δ 164.7, 162.1, 146.8, 145.4, 142.4, 135.7, 120.3, 28.0, 27.7, 11.1, 11.0.

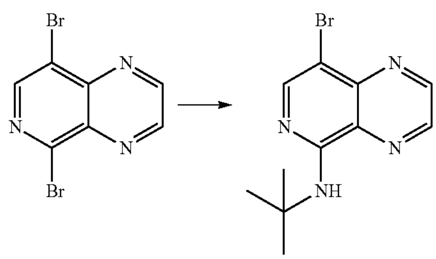 [SMILES: Brc1cnc(Br)c2nccnc12 ; CC(C)(C)Nc1ncc(Br)c2nccnc12]

HSL524: 8-bromo-N-(tert-butyl)pyrido[3,4-b]pyrazin-5-amine

To a pressure tube fitted with a magnetic stir bar, 5,8-dibromopyrido[3,4-b]pyrazine (83 mg, 0.290 mmol, 1 eq) in ethanol (2 mL) were added. Tert-butylamine (63.5 mg, 0.870 mmol, 3 eq) was then added and reaction was capped and moved to 110° C. The reaction was then allowed to run for 16 hours. Following 16 hours, 3 additional equivalents of tert-butylamine was then added. The reaction then 3 days. Crude product was then cooled to room temperature and concentrated under reduced pressure. Pure product was obtained via column chromatography (1:1 Hex/DCM). Yield=57% TLC Rf=0.3 (1:1 Hex/DCM) $^1$H NMR (500 MHz, DMSO-$d_6$) δ 9.12 (d, J=2.0 Hz, 1H), 8.84 (d, J=1.9 Hz, 1H), 8.35 (s, 1H), 7.08 (s, 1H), 1.50 (s, 9H). $^{13}$C NMR (126 MHz, DMSO) δ 155.7, 150.4, 147.6, 144.3, 143.8, 130.1, 103.7, 52.0, 28.7.

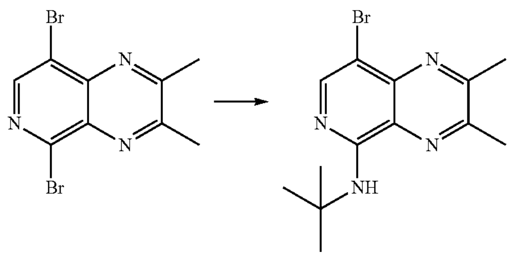 [SMILES: Cc1nc2c(Br)cnc(Br)c2nc1C ; Cc1nc2c(Br)cnc(NC(C)(C)C)c2nc1C]

HSL524: 8-bromo-N-(tert-butyl)-2,3-dimethylpyrido[3,4-b]pyrazin-5-amine

To a pressure tube fitted with a magnetic stir bar, 5,8-dibromo-2,3-dimethylpyrido[3,4-b]pyrazine (147 mg, 0.468 mmol, 1 eq) in ethanol (3 mL) was added. Tert-butylamine (106 mg, 1.4 mmol, 3 eq) were then added and reaction was capped and moved to 110° C. The reaction was then allowed to run for 16 hours. Following 16 hours, 3 additional equivalents of tert-butylamine was then added. The reaction then run for 3 days. Crude product was then cooled to room temperature and concentrated under reduced pressure. Pure product was obtained via column chromatography (1:1 Hex/DCM). Yield=16.6% TLC Rf=0.5 (25% EA/Hex) $^1$H NMR (500 MHz, DMSO-$d_6$) δ 8.23 (s, 1H), 6.83 (s, 1H), 2.68 (s, 3H), 2.66 (s, 3H), 1.50 (s, 9H). $^{13}$C NMR (126 MHz, DMSO) δ 159.4, 155.1, 153.3, 146.2, 141.6, 127.5, 103.6, 51.7, 28.8, 23.4, 22.8.

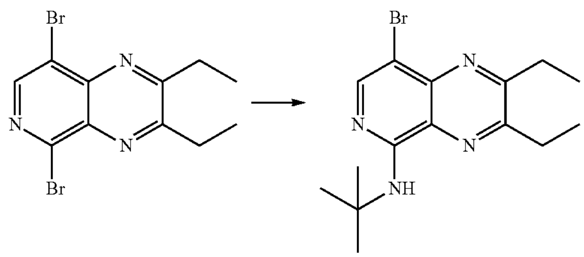 [SMILES: CCc1nc2c(Br)cnc(Br)c2nc1CC ; CCc1nc2c(Br)cnc(NC(C)(C)C)c2nc1CC]

HSL525: 8-bromo-N-(tert-butyl)-2,3-diethylpyrido[3,4-b]pyrazin-5-amine

To a pressure tube fitted with a magnetic stir bar, 5,8-dibromo-2,3-diethylpyrido[3,4-b]pyrazine (153 mg, 0.443 mmol, 1 eq) in ethanol (3 mL) were added. Tert-butylamine (97.1 mg, 1.433 mmol, 3 eq) was then added and reaction was capped and moved to 110° C. The reaction was then allowed to run for 16 hours. Following 16 hours, 3 additional equivalents of tert-butylamine was then added. The reaction then run for 3 days. Crude product was then cooled to room temperature and concentrated under reduced pressure. Pure product was obtained via column chromatography (1:1 Hex/DCM). Yield=14% TLC Rf=0.7 (25% EA/Hex) $^1$H NMR (500 MHz, DMSO-$d_6$) δ 8.25 (s, 1H), 6.82 (s, 1H), 3.02 (dq, J=12.9, 7.3 Hz, 4H), 1.51 (s, 9H), 1.34-1.30 (m, 6H).

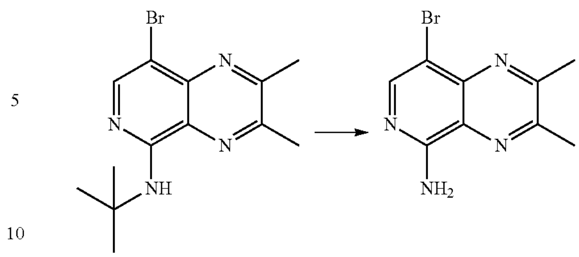

HSL544: 8-bromo-2,3-dimethylpyrido[3,4-b]pyrazin-5-amine

To a pressure tube fitted with a magnetic stir bar, 8-bromo-N-(tert-butyl)-2,3-dimethylpyrido[3,4-b]pyrazin-5-amine (88 mg, 0.285 mmol) in concentrated HCl (1.0 mL) were added. The reaction was capped and moved to 80° C. and run for 2 hours. The reaction was then diluted with water (50 mL) and neutralized using saturated sodium bicarbonate solution. Product was then extracted with ethyl acetate (3×100 mL). Organic layers were dried over anhydrous sodium sulfate, filtered, and concentrated under reduced pressure. Pure product was obtained via column chromatography (1:1 EA/Hex). Yield=62.6%; TLC Rf=0.5 (1:1 EA/Hex). $^1$H NMR (500 MHz, DMSO-$d_6$) δ 8.14 (s, 1H), 7.16 (s, 2H), 2.68 (s, 3H), 2.67 (s, 3H). $^{13}$C NMR (126 MHz, DMSO) δ 164.6, 163.1, 158.4, 151.4, 147.1, 132.0, 108.4, 28.5, 27.8.

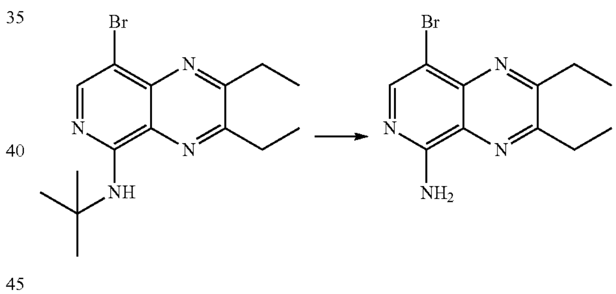

HSL545: 8-bromo-2,3-diethylpyrido[3,4-b]pyrazin-5-amine

To a pressure tube fitted with a magnetic stir bar, 8-bromo-2,3-diethylpyrido[3,4-b]pyrazin-5-amine (163 mg, 0.445 mmol) in concentrated HCl (1.5 mL) were added. The reaction was capped and moved to 80° C. and run for 2 hours. The reaction was then diluted with water (50 mL) and neutralized using saturated sodium bicarbonate solution. Product was then extracted with ethyl acetate (3×100 mL). Organic layers were dried over anhydrous sodium sulfate, filtered, and concentrated under reduced pressure. Pure product was obtained via column chromatography (1:1 EA/Hex). Yield=68.2%; TLC Rf=0.45 (1:1 EA/Hex). $^1$H NMR (500 MHz, DMSO-$d_6$) δ 8.16 (s, 1H), 7.14 (s, 2H), 3.01 (dq, J=16.0, 7.3 Hz, 4H), 1.33 (q, J=7.3 Hz, 6H). $^{13}$C NMR (126 MHz, DMSO) δ 162.5, 158.2, 156.6, 146.7, 141.7, 126.7, 103.8, 27.9, 27.2, 11.8, 11.7.

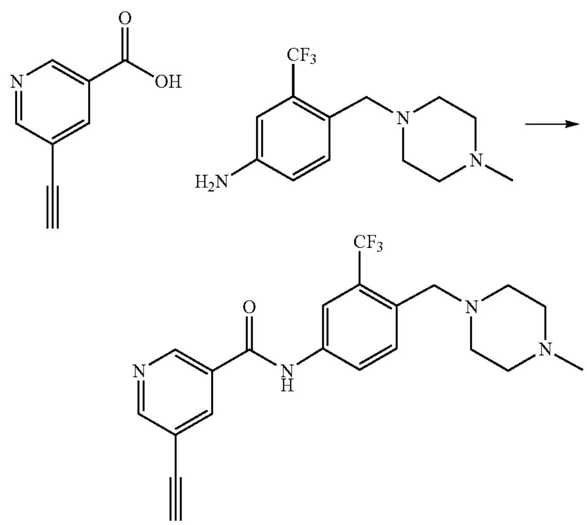

5-ethynyl-N-(4-((4-methylpiperazin-1-yl)methyl)-3-(trifluoromethyl)phenyl)nicotinamide 5-Ethynylnicotinic acid (1 g, 6.8 mmol, 1 equiv) and HATU (1.8 g, 8.2 mmol, 1.2 equiv) were added to a round bottom. Air was vacuumed out and vessel was then protected with a balloon of argon gas. DMF (8 mL) was then added and the reaction was cooled to 0° C. DIPEA (2.6 g, 2.4 mmol, 3 equiv) was then added. Upon addition of 4-((4-methylpiperazin-1-yl)methyl)-3-(trifluoromethyl)aniline (1.8 g, 6.8 mmol, 1 equiv), the reaction was then moved to 55° C. and allowed to run over night. Reaction was then concentrated under reduced pressure and purified via column chromatography (10% MeOH/DCM). Yield: 94.5%

$^1$H NMR (500 MHz, DMSO-$d_6$) δ 10.70 (s, 1H), 9.07 (d, J=2.1 Hz, 1H), 8.86 (d, J=2.0 Hz, 1H), 8.41 (t, J=2.1 Hz, 1H), 8.17 (d, J=2.3 Hz, 1H), 8.00 (dd, J=8.5, 2.2 Hz, 1H), 7.71 (d, J=8.5 Hz, 1H), 4.58 (s, 1H), 3.56 (s, 2H), 2.41 (s, 8H), 2.22 (s, 3H). $^{13}$C NMR (126 MHz, DMSO) δ 163.8, 154.8, 148.9, 138.4, 138.3, 132.9, 131.8, 130.2, 128.1, 127.8, 125.8, 124.0, 123.6, 118.9, 117.7, 85.6, 80.2, 57.8, 54.9, 52.7, 45.7.

General Procedures for the Synthesis of HSND Analogs:

General Procedure for the Amide Coupling

To a solution of amine (1 mmol) and carboxylic acid substrate (1.1 mmol) in DMF (4 mL), HATU (1.3 equiv) and DIPEA (3 equiv) were added. Reaction was allowed to stir at 60° C. for an overnight. After completion reaction was concentrated and extracted with ethyl acetate and water, washed with brine. Collected organic layer dried over sodium sulphate, concentrated and purified via silica gel chromatography to afford the pure desired compound (Hexanes/Ethyl acetate 90:10 to 50:50).

General Procedure for the Sonogashira Coupling

In a 25 mL round bottom flask containing bromo substrate (0.5 mmol), alkyne substrate (0.6 mmol), $PdCl_2(PPh_3)_2$ (3 mol %), XPhos (2 mol %), $Cs_2CO_3$ (3 equiv) and CuI (1 mol %), anhydrous DMF (3 mL) and DIPEA (1.65 mL) was added under inert condition. Reaction mixture allowed to stir at 60° C. for an overnight. After completion reaction mixture was concentrated and extracted with ethyl acetate. Collected organic layer dried with sodium sulfate, concentrated and purified via silica gel column chromatography to yield the desired product using DCM/MeOH (95:5) as a solvent system or (Hexanes/Ethyl acetate 90:10 to 0:100).

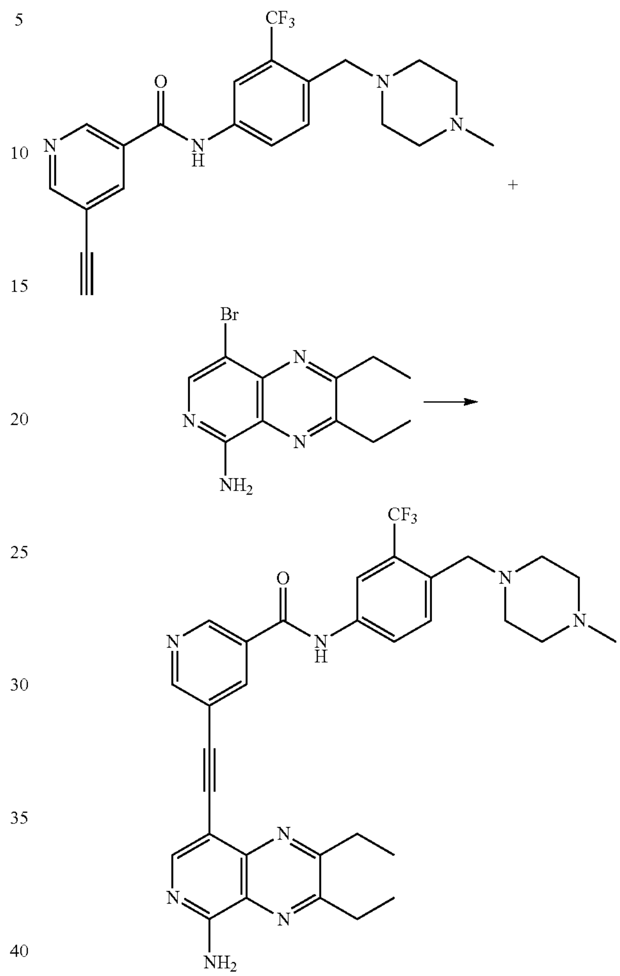

HSND-15

HSND-15: 5-((5-Amino-2,3-diethylpyrido[3,4-b]pyrazin-8-yl)ethynyl)-N-(4-((4-methylpiperazin-1-yl)methyl)-3-(trifluoromethyl)phenyl)nicotinamide Yellow solid, yield: 27% $^1$H NMR (500 MHz, DMSO-$d_6$) δ 10.80 (s, 1H), 9.05 (d, J=2.2 Hz, 1H), 8.89 (d, J=2.0 Hz, 1H), 8.44 (t, J=2.1 Hz, 1H), 8.33 (s, 1H), 8.20 (d, J=2.2 Hz, 1H), 8.03 (dd, J=8.4, 2.2 Hz, 1H), 7.72 (d, J=8.5 Hz, 1H), 7.53 (s, 2H), 3.56 (s, 2H), 3.07 (q, J=7.3 Hz, 2H), 3.01 (q, J=7.3 Hz, 2H), 2.14 (s, 3H), 1.37 (dt, J=14.5, 7.3 Hz, 6H).

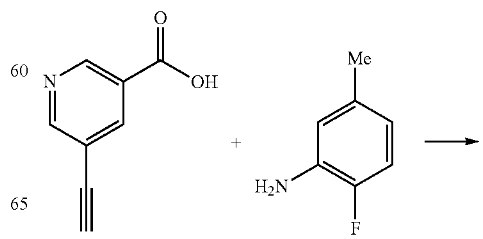

-continued

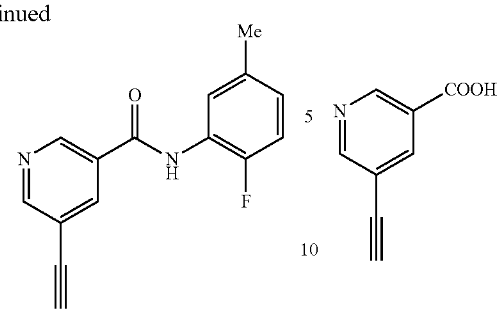

5-ethynyl-N-(2-fluoro-5-methylphenyl)nicotinamide

$^1$H NMR (500 MHz, Methanol-$d_4$) δ 9.04 (s, 1H), 8.81 (s, 1H), 8.40 (s, 1H), 7.57 (d, J=7.1 Hz, 1H), 7.08 (d, J=7.3 Hz, 2H), 4.08-3.80 (m, 1H), 2.34 (d, J=5.4 Hz, 3H).

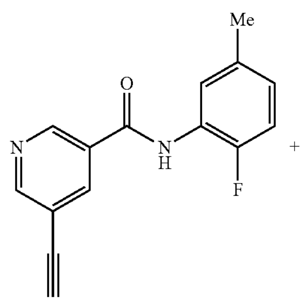

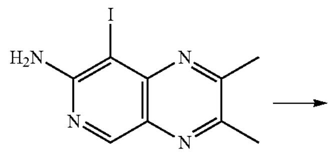

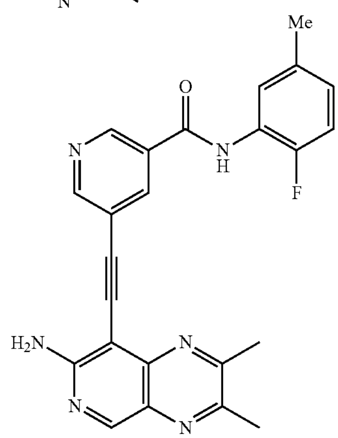

HSND65

HSND65: 5-((7-Amino-2,3-dimethylpyrido[3,4-b]pyrazin-8-yl)ethynyl)-N-(2-fluoro-5-methylphenyl)nicotinamide Yellow solid, yield 33%. $^1$H NMR (500 MHz, Methanol-$d_4$) δ 9.03 (dd, J=4.6, 2.0 Hz, 2H), 8.83 (s, 1H), 8.62 (d, J=2.1 Hz, 1H), 7.61 (d, J=7.3 Hz, 1H), 7.13-7.05 (m, 2H), 2.76 (s, 3H), 2.66 (s, 3H), 2.36 (s, 3H).

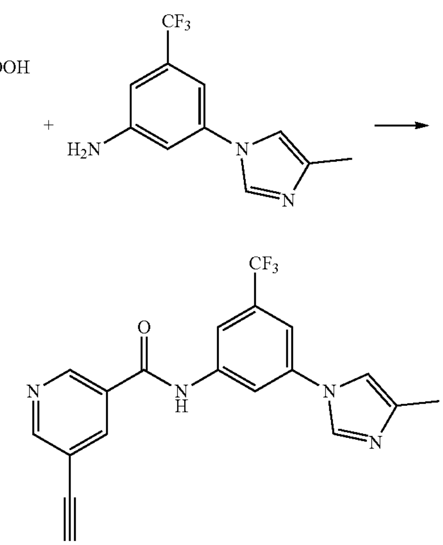

5-Ethynyl-N-(3-(4-methyl-1H-imidazol-1-yl)-5-(trifluoromethyl)phenyl)nicotinamide To a solution of amine (1 mmol) and carboxylic acid substrate (1.1 mmol) in dichloromethane (4 mL), HATU (1.3 equiv) and DIPEA (3 equiv) were added. Reaction was allowed to stir at 60° C. for an overnight. After completion reaction was concentrated and extracted with ethyl acetate and water, washed with brine. Collected organic layer dried over sodium sulphate, concentrated and purified via silica gel chromatography to afford the pure desired compound (Hexanes/Ethyl acetate 90:10 to 50:50).

$^1$H NMR (500 MHz, Methanol-$d_4$) δ 9.12-9.03 (m, 1H), 8.86-8.76 (m, 1H), 8.50-8.39 (m, 1H), 8.23 (d, J=2.3 Hz, 1H), 8.15-8.07 (m, 2H), 7.70-7.60 (m, 1H), 7.45-7.32 (m, 1H), 2.81 (s, 2H), 2.27 (s, 3H).

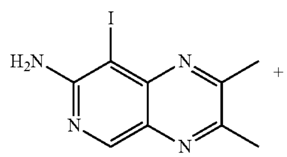

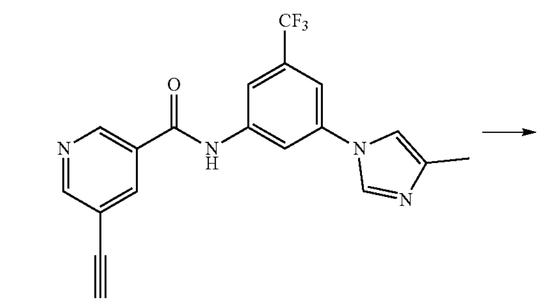

-continued

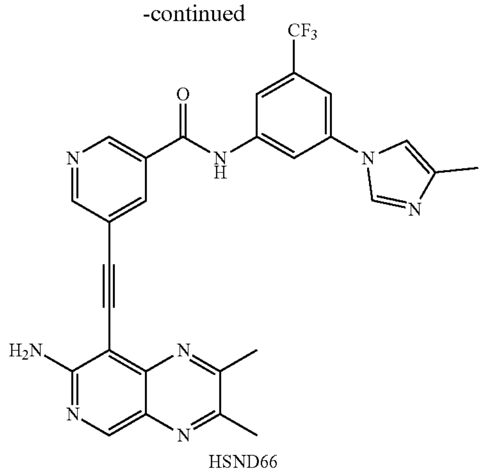

HSND66

HSND66: 5-((7-Amino-2,3-dimethylpyrido[3,4-b]pyrazin-8-yl)ethynyl)-N-(3-(4-methyl-1H-imidazol-1-yl)-5-(trifluoromethyl)phenyl)nicotinamide Yellow solid, yield: 28%. $^{1}$H NMR (500 MHz, Methanol-$d_4$) δ 9.04 (dd, J=13.4, 2.1 Hz, 2H), 8.80 (s, 1H), 8.63 (t, J=2.1 Hz, 1H), 8.25 (d, J=2.0 Hz, 1H), 8.14 (d, J=1.5 Hz, 1H), 8.09 (s, 2H), 7.65 (q, J=2.5, 1.8 Hz, 1H), 7.38 (t, J=1.3 Hz, 1H), 2.75 (s, 3H), 2.65 (s, 3H), 2.27 (s, 3H).

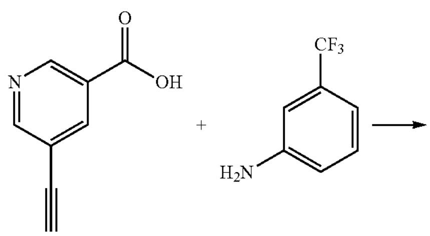

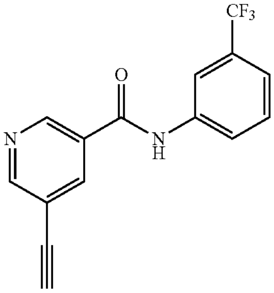

5-Ethynyl-N-(3-(trifluoromethyl)phenyl)nicotinamide $^{1}$H NMR (500 MHz, Methanol-$d_4$) δ 9.05 (d, J=2.3 Hz, 1H), 8.86-8.76 (m, 1H), 8.41 (q, J=1.7 Hz, 1H), 8.15 (t, J=2.3 Hz, 1H), 7.93 (dd, J=8.1, 2.3 Hz, 1H), 7.60-7.48 (m, 1H), 7.48-7.41 (m, 1H), 3.91 (s, 1H).

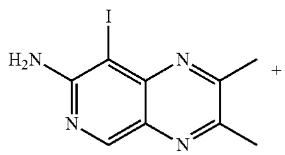

+

-continued

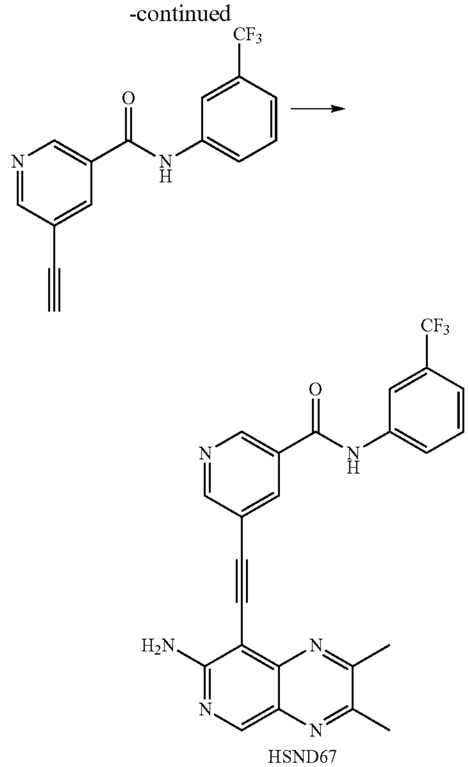

HSND67

HSND67: 5-((7-Amino-2,3-dimethylpyrido[3,4-b]pyrazin-8-yl)ethynyl)-N-(3-(trifluoromethyl)phenyl)nicotinamide Yellow solid, yield: 45%. $^{1}$H NMR (500 MHz, Methanol-$d_4$) δ 9.04 (d, J=2.3 Hz, 2H), 8.83 (d, J=1.6 Hz, 1H), 8.63 (d, J=2.2 Hz, 1H), 8.20 (s, 1H), 7.97 (d, J=8.2 Hz, 1H), 7.58 (t, J=8.1 Hz, 1H), 7.46 (d, J=7.8 Hz, 1H), 2.76 (s, 3H), 2.67 (s, 3H).

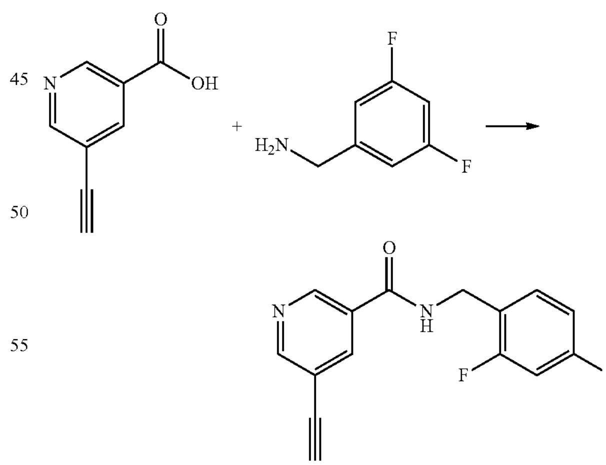

N-(2,4-difluorobenzyl)-5-ethynylnicotinamide $^{1}$H NMR (500 MHz, Methanol-$d_4$) δ 8.94 (d, J=2.2 Hz, 1H), 8.75 (d, J=2.0 Hz, 1H), 8.29 (t, J=2.1 Hz, 1H), 7.44 (td, J=8.8, 6.4 Hz, 1H), 7.09-6.83 (m, 2H), 4.59 (s, 2H), 3.89 (s, 1H).

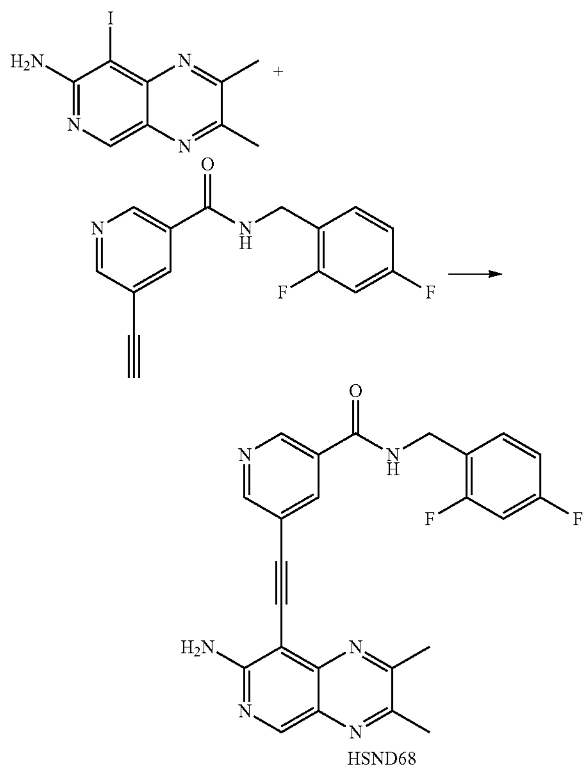

HSND68

HSND 68: 5-((7-Amino-2,3-dimethylpyrido[3,4-b]pyrazin-8-yl)ethynyl)-N-(2,4-difluorobenzyl)nicotinamide Yellow solid, yield: 31%. $^1$H NMR (500 MHz, Methanol-$d_4$) δ 9.02-8.89 (m, 2H), 8.80 (s, 1H), 8.48 (t, J=2.0 Hz, 1H), 7.48 (td, J=8.8, 6.5 Hz, 1H), 7.01-6.90 (m, 2H), 4.62 (s, 2H), 2.74 (s, 3H), 2.65 (s, 3H).

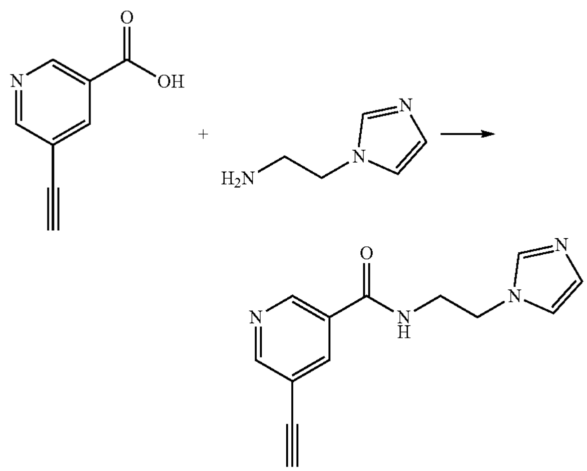

N-(2-(1H-imidazol-1-yl)ethyl)-5-ethynylnicotinamide $^1$H NMR (500 MHz, Methanol-$d_4$) δ 8.86 (d, J=2.2 Hz, 1H), 8.74 (d, J=2.0 Hz, 1H), 8.20 (t, J=2.1 Hz, 1H), 7.67 (s, 1H), 7.16 (s, 1H), 6.98 (s, 1H), 4.27 (t, J=6.0 Hz, 2H), 3.90 (s, 1H), 3.73 (t, J=6.0 Hz, 2H).

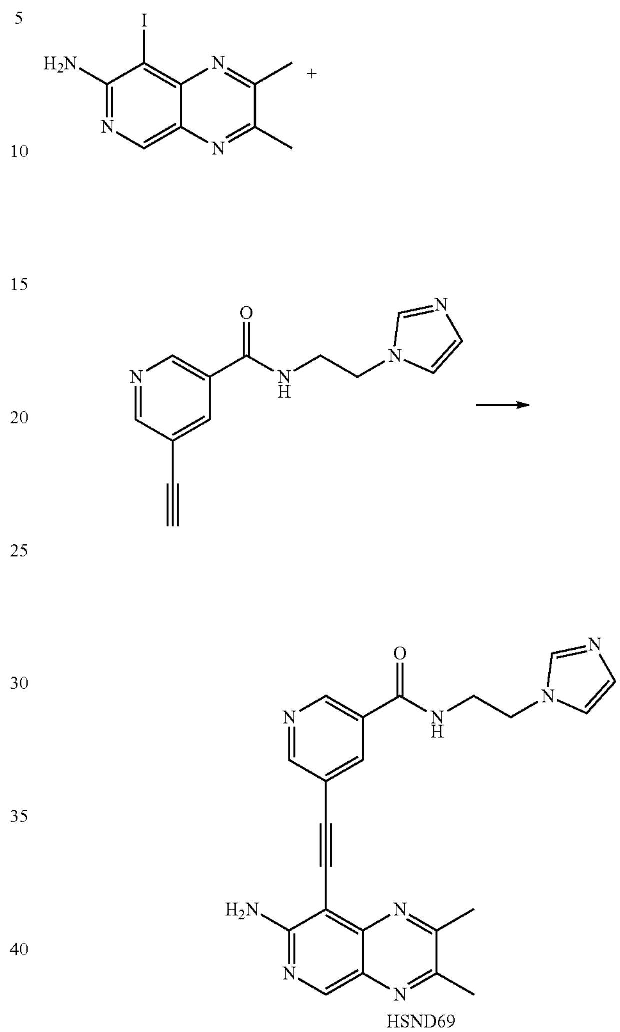

HSND69

HSND69: N-(2-(1H-imidazol-1-yl)ethyl)-5-((7-amino-2,3-dimethylpyrido[3,4-b]pyrazin-8-yl)ethynyl)nicotinamide Yellow solid, yield: 23%. $^1$H NMR (500 MHz, Methanol-$d_4$) δ 9.05 (d, J=2.2 Hz, 2H), 8.84 (s, 1H), 8.63 (t, J=2.1 Hz, 1H), 8.29 (d, J=2.6 Hz, 1H), 8.01 (dd, J=8.6, 2.6 Hz, 1H), 7.62 (d, J=8.7 Hz, 1H), 3.34 (s, 2H), 2.77 (s, 3H), 2.67 (s, 3H).

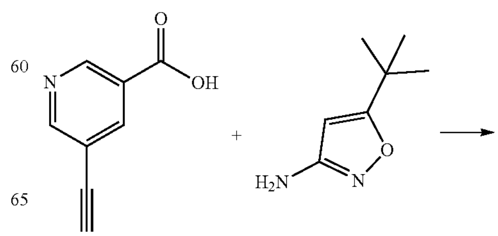

-continued

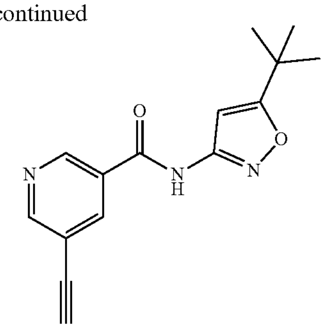

N-(5-(tert-butyl)isoxazol-3-yl)-5-ethynylnicotinamide $^1$H NMR (500 MHz, Methanol-$d_4$) δ 9.05 (d, J=2.2 Hz, 1H), 8.82 (d, J=2.0 Hz, 1H), 8.41 (t, J=2.1 Hz, 1H), 6.69 (s, 1H), 3.93 (s, 1H), 1.37 (s, 9H).

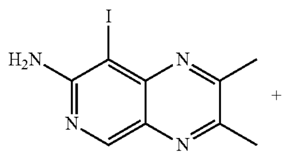

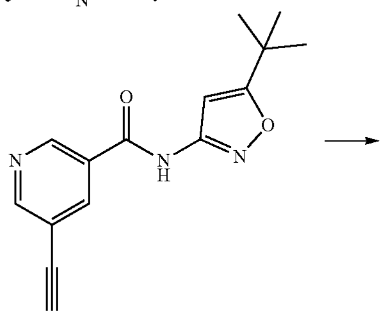

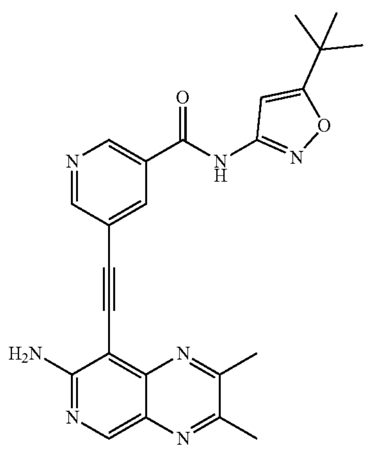

HSND70

HSND70: 5-((7-Amino-2,3-dimethylpyrido[3,4-b]pyrazin-8-yl)ethynyl)-N-(5-(tert-butyl)isoxazol-3-yl)nicotinamide Yellow solid, yield: 30%. $^1$H NMR (500 MHz, Methanol-$d_4$) δ 9.02 (s, 2H), 8.80 (s, 1H), 8.59 (s, 1H), 6.72 (s, 1H), 2.75 (s, 3H), 2.65 (s, 3H), 1.38 (s, 9H).

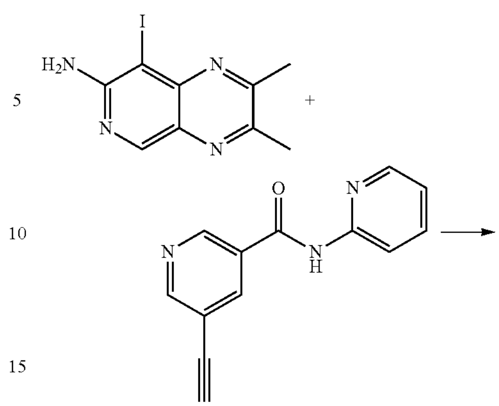

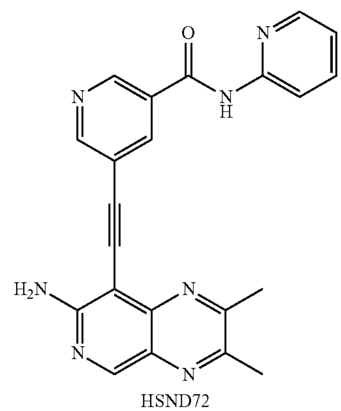

HSND72

HSND72: 5-((7-Amino-2,3-dimethylpyrido[3,4-b]pyrazin-8-yl)ethynyl)-N-(pyridin-2-yl)nicotinamide Yellow solid, yield: 24%. $^1$H NMR (500 MHz, Methanol-$d_4$) δ 9.05 (dd, J=6.1, 2.1 Hz, 3H), 8.83 (s, 1H), 8.65 (t, J=2.1 Hz, 1H), 8.40-8.36 (m, 1H), 8.24 (dd, J=7.7, 1.6 Hz, 1H), 7.88-7.83 (m, 1H), 7.22-7.16 (m, 1H), 2.77 (s, 3H), 2.67 (s, 3H).

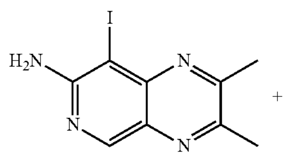

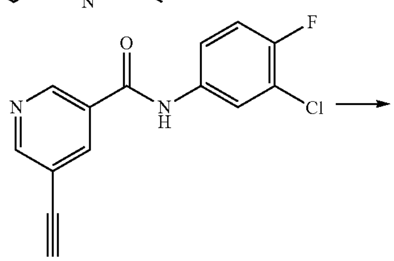

-continued

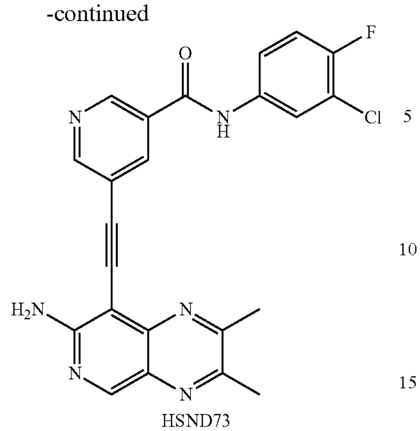

HSND73

HSND73: 5-((7-Amino-2,3-dimethylpyrido[3,4-b]pyrazin-8-yl)ethynyl)-N-(3-chloro-4-fluorophenyl)nicotinamide Yellow solid, yield: 21%. $^{1}$H NMR (500 MHz, DMSO-$d_6$) δ 10.73 (s, 1H), 9.04 (dd, J=12.3, 2.1 Hz, 2H), 8.86 (s, 1H), 8.58 (t, J=2.1 Hz, 1H), 8.08 (dd, J=6.8, 2.5 Hz, 1H), 7.72 (ddd, J=9.1, 4.3, 2.6 Hz, 1H), 7.45 (t, J=9.1 Hz, 1H), 7.05 (s, 2H), 2.68 (s, 3H), 2.59 (s, 3H).

GI50 Determination

According to the National Cancer Institute, Bethesda, Maryland (the protocol of the Drug Evaluation Branch), the effects of compounds are measured as follows: Cell suspensions are diluted to a target cell density of 5000-40,000 cells per well (based on cell growth characteristics) in a 96-well microtiter plates. The test compounds were evaluated at five concentrations (10-fold dilutions) with the highest concentration being 100 μM. The incubation period was 48 h under 5% carbon dioxide atmosphere and 100% humidity. A sulforhodamine B assay was used to assay the cells. Optical densities of the wells were read by a plate reader the optical densities were processed into GI50 (the concentration that causes 50% growth inhibition).

The NCI renamed the IC50 value, the concentration of compound that causes 50% growth inhibition, as follows.

GI50=100×(T−T0)/(C−T0)=50, where T=the optical density of the test well after a 48-h period of exposure to test drug, T0=the optical density at time zero, C=the control optical density. The control is the well not treated with test agent (https://dtp.cancer.gov/databases_tools/docs/compare/compare_methodology.htm).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

We claim:

1. A compound selected from the group consisting of:

1

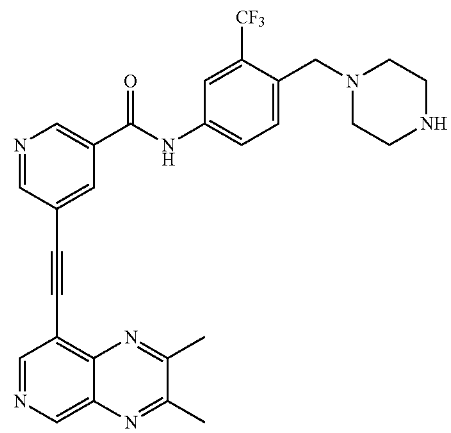

2 (HSL211)

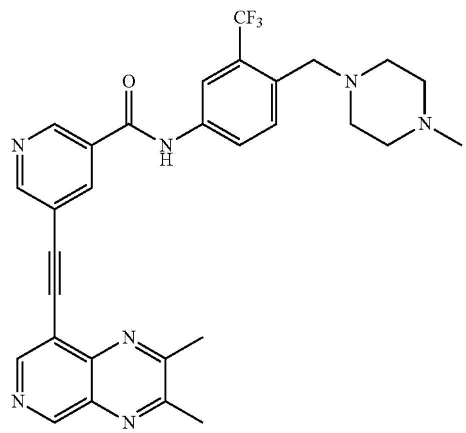

3

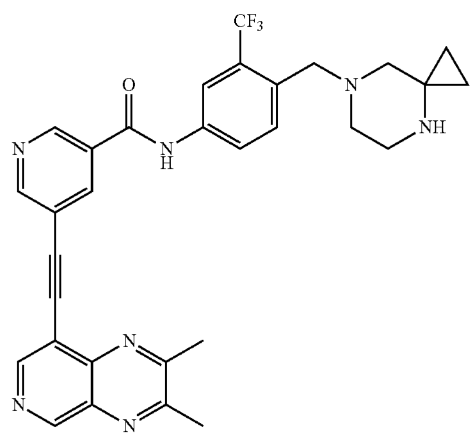

-continued
4
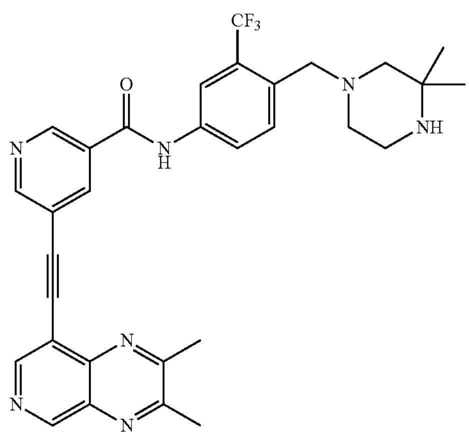
1b1
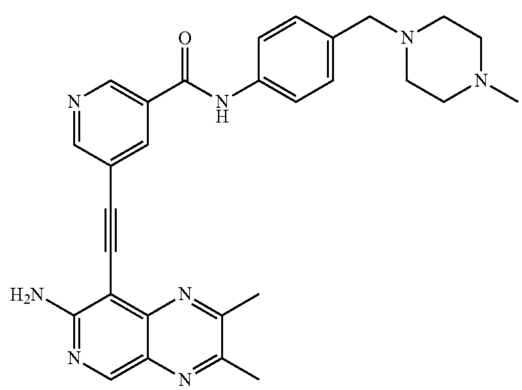
1b2
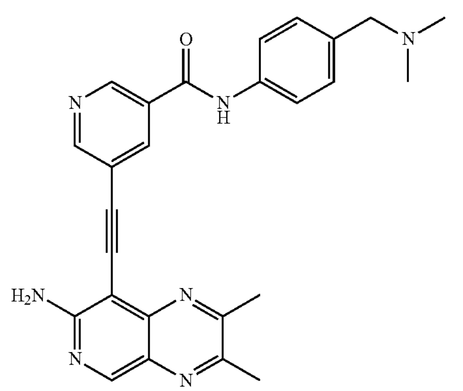
1b3
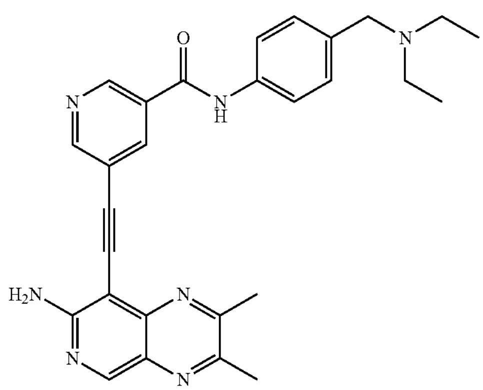
-continued
1b4
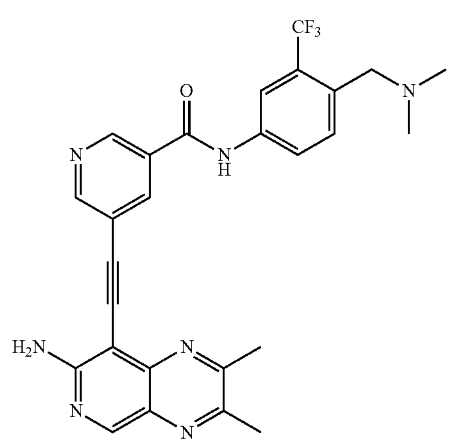
1b5
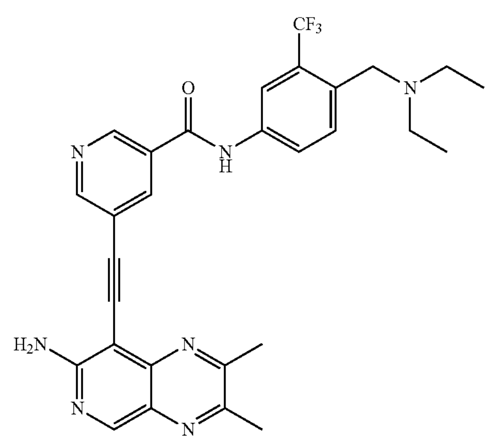
1b6
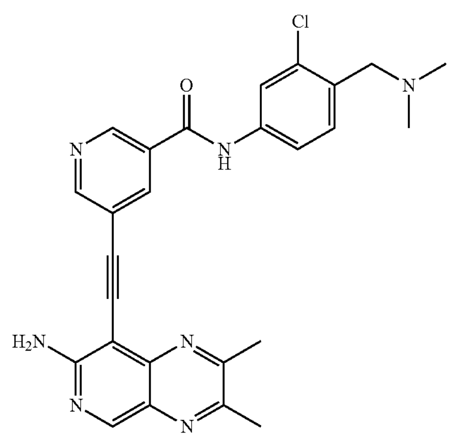

-continued
1b7
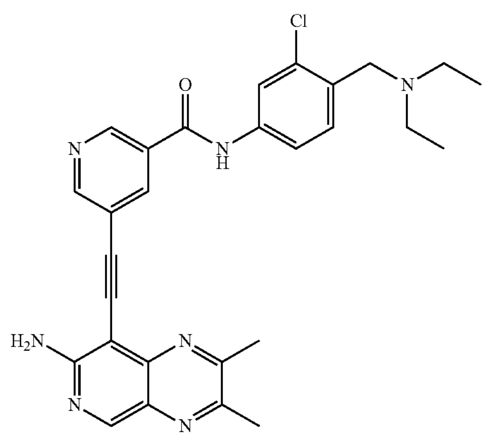
1b8
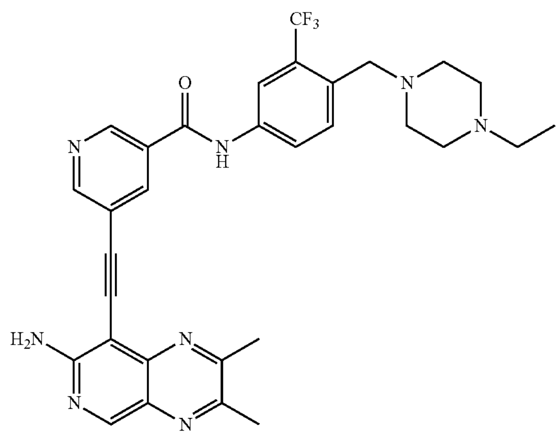
1b
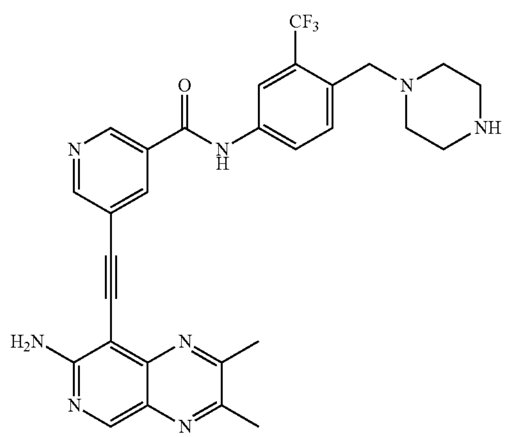
-continued
2b (HSL476)
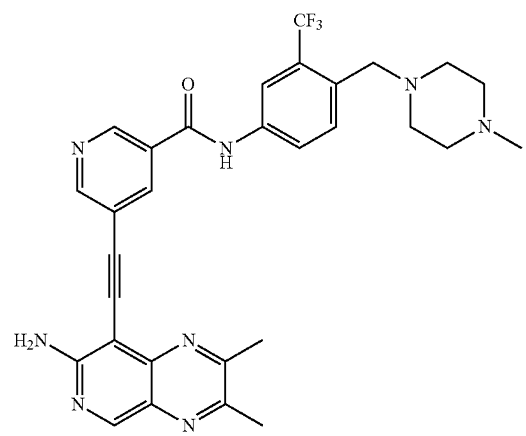
3b
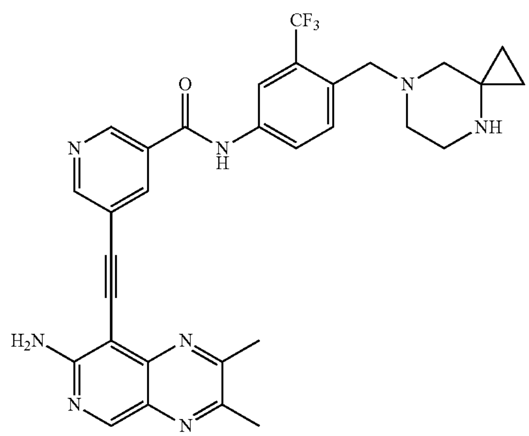
4b
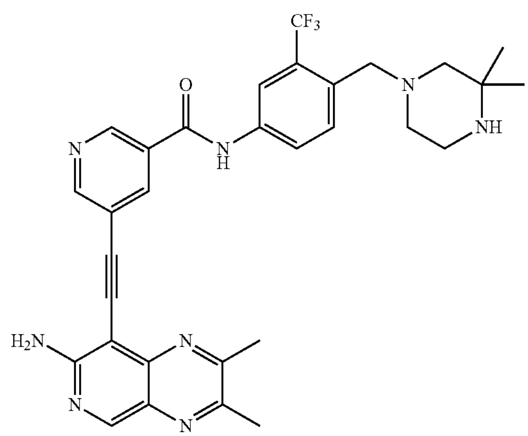

-continued
1b9
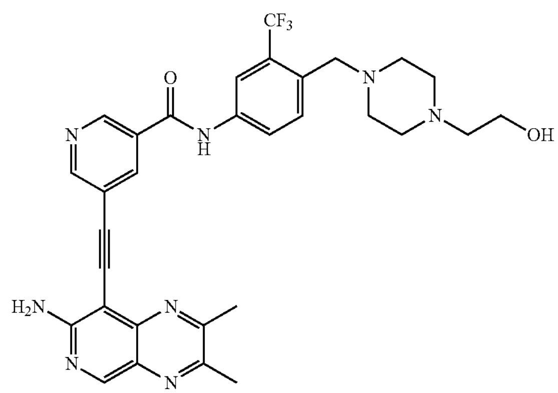
1b10
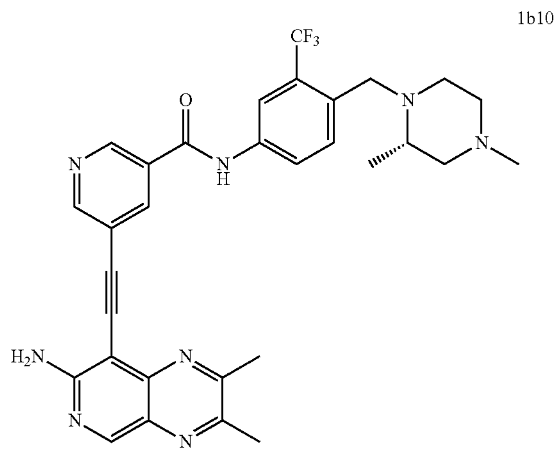
1b11
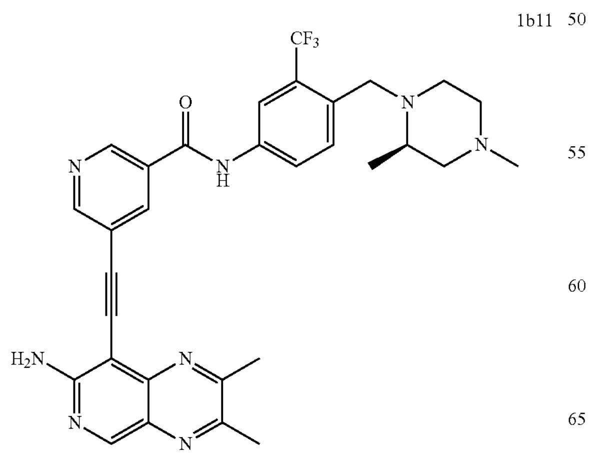
-continued
1b12
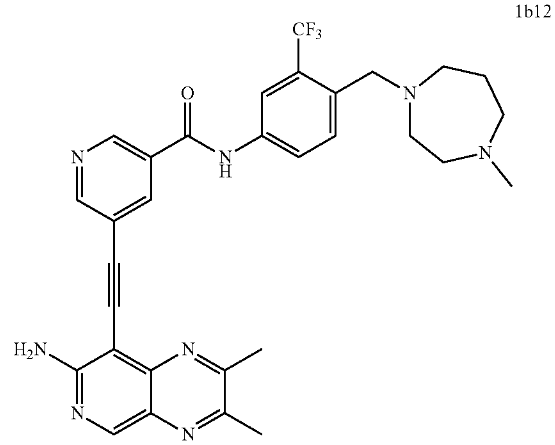
1b13
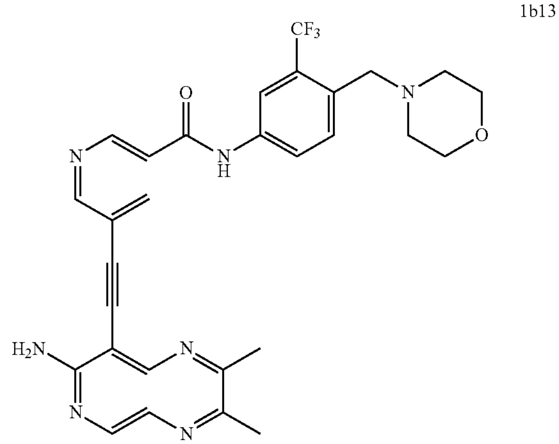
1b14
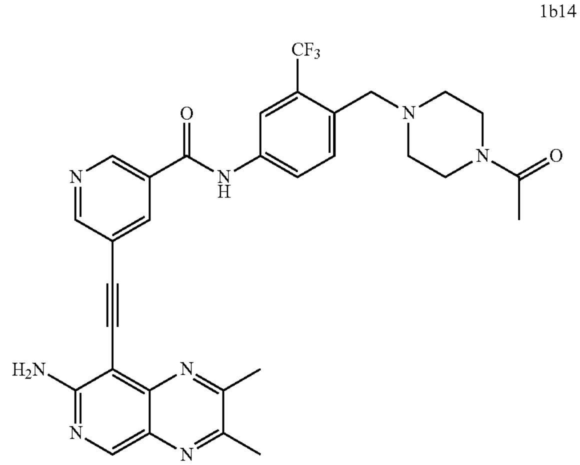

-continued
1b14
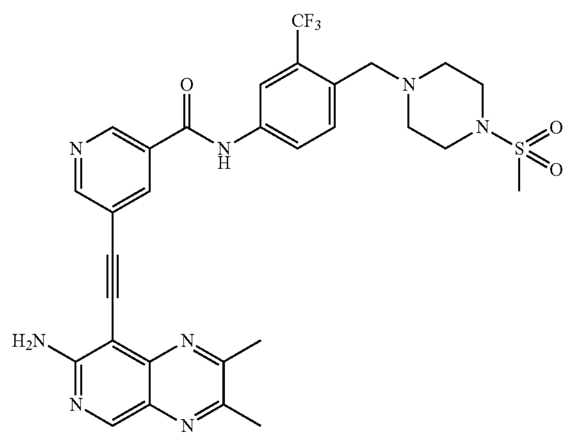
1b14
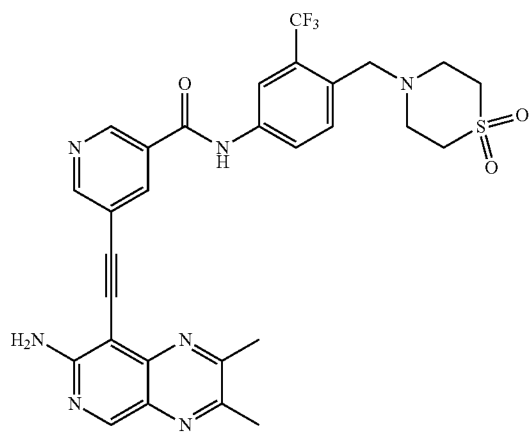
1b15
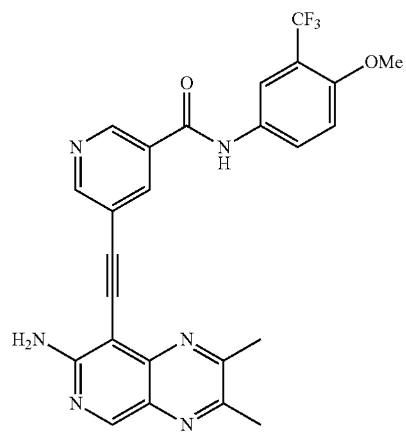
-continued
1b16
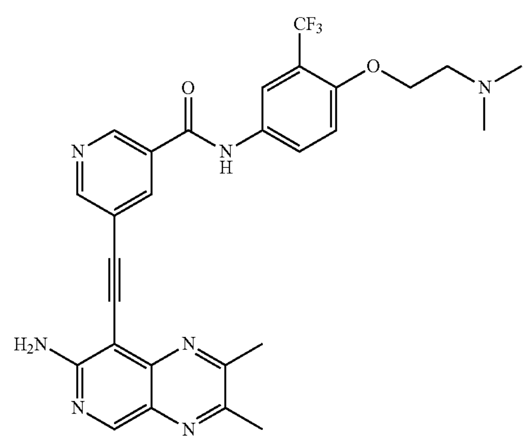
1b17
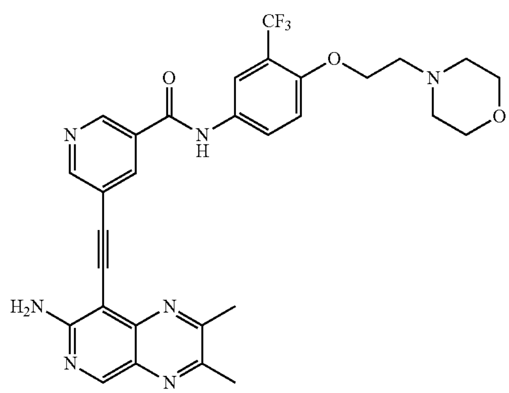
1b18
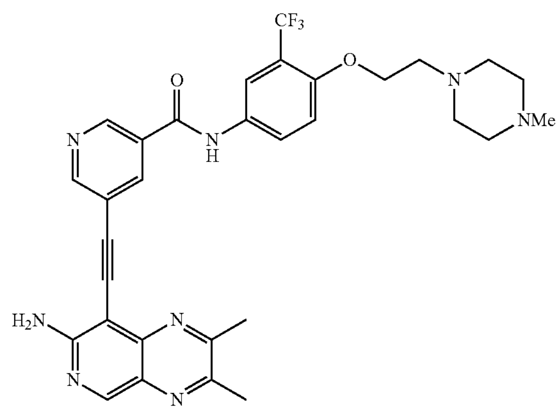
1b19
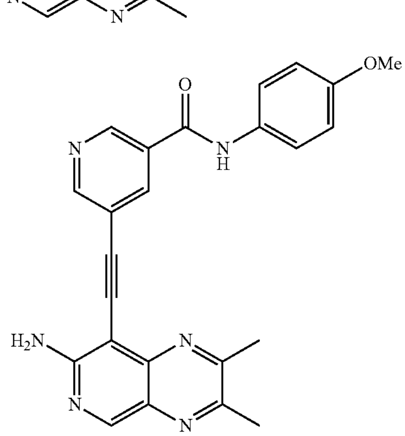

-continued
1b20
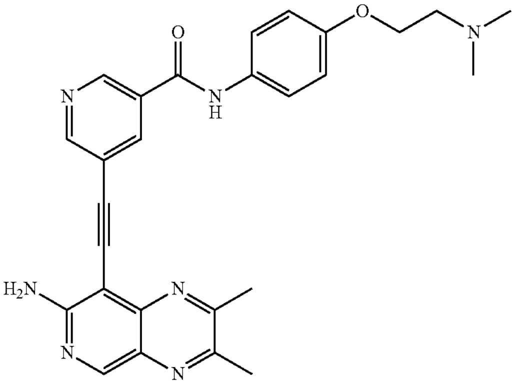
1b21
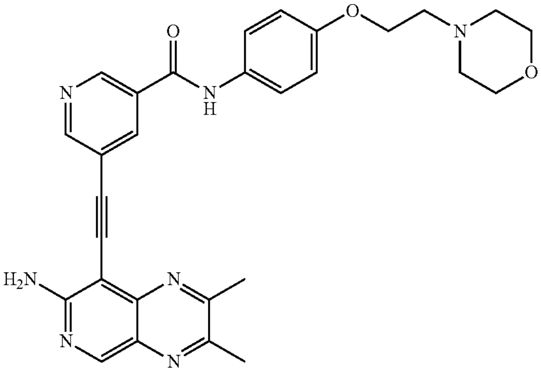
1b22
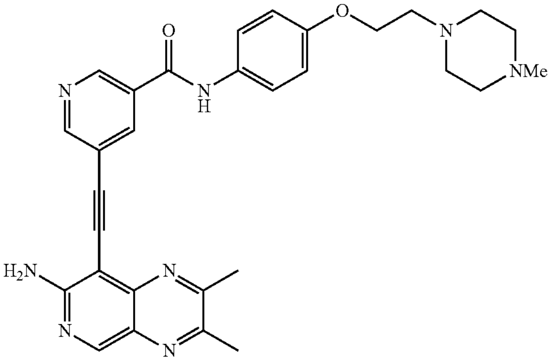
1b23
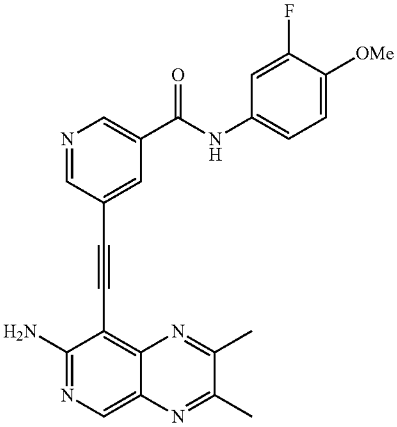
-continued
1b24
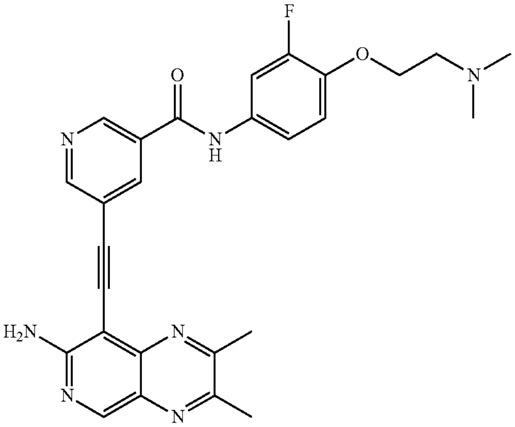
1b25
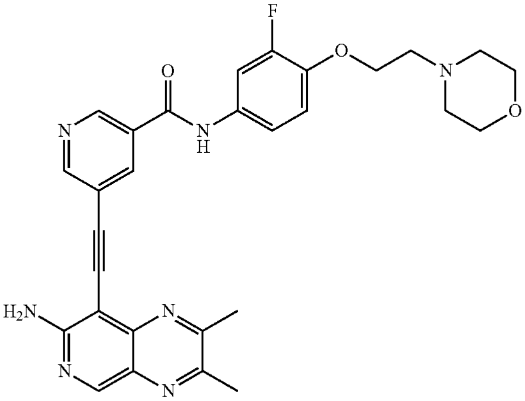
1b26
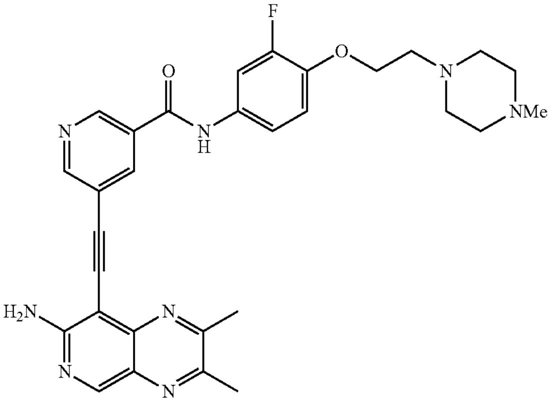

-continued
1b27
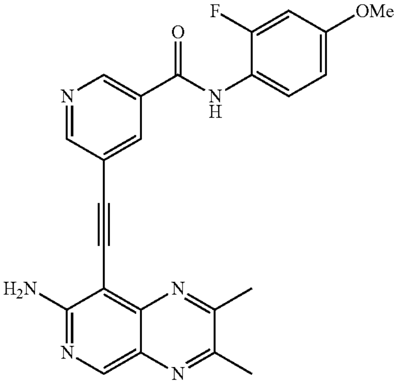
1b28
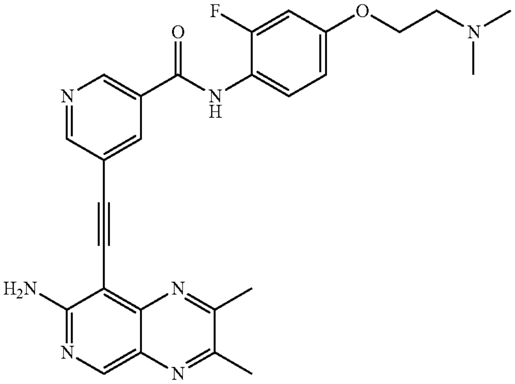
1b29
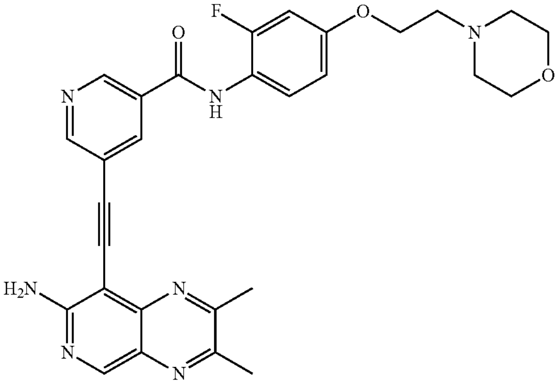
1b30
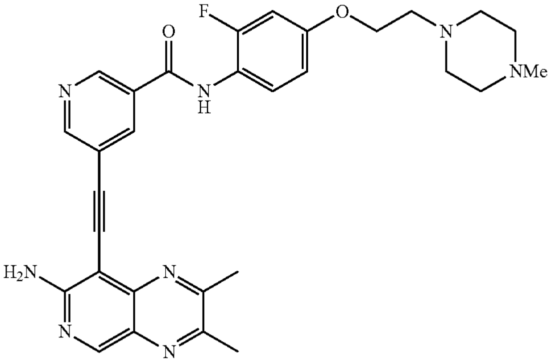
-continued
1c
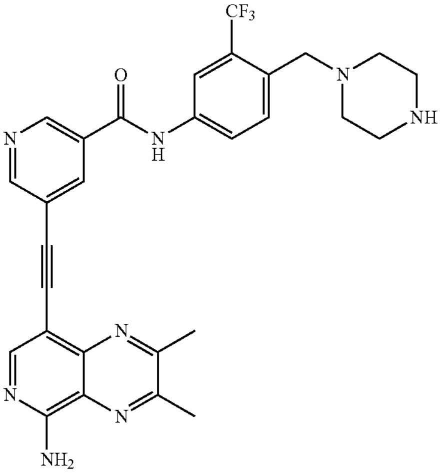
2c
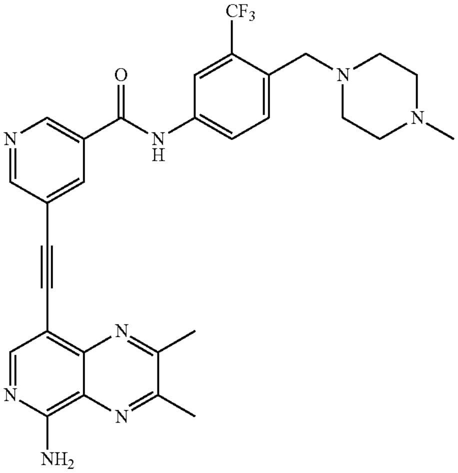
3c
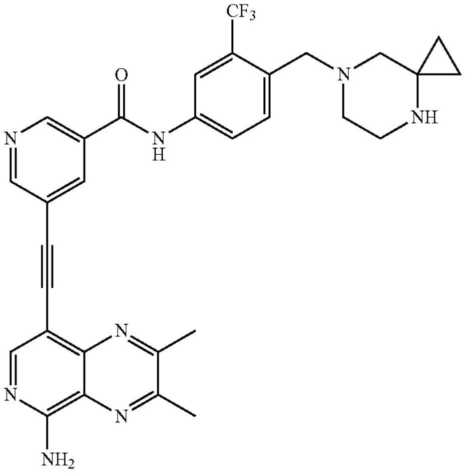

-continued
4c
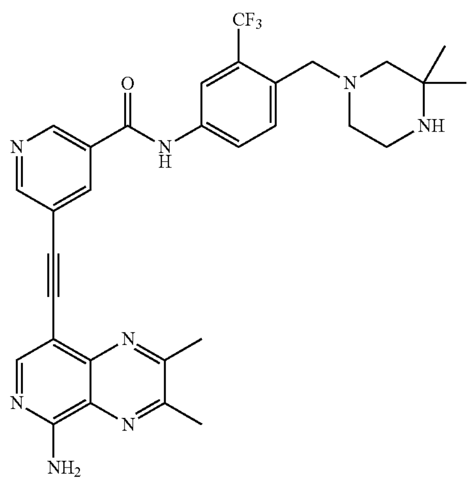
5
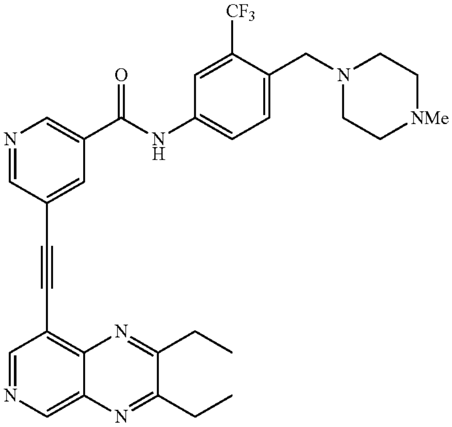
6
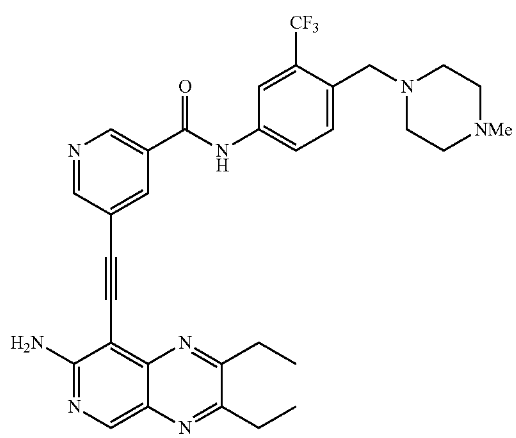
-continued
7
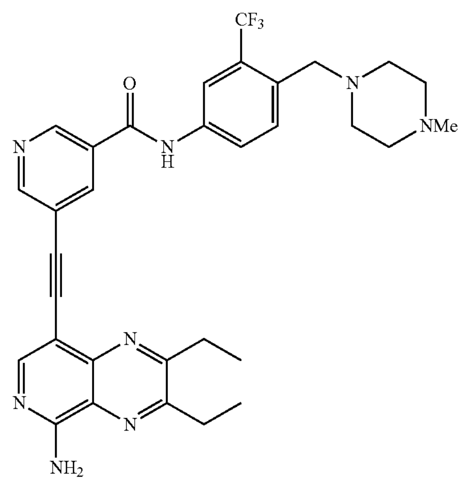
8
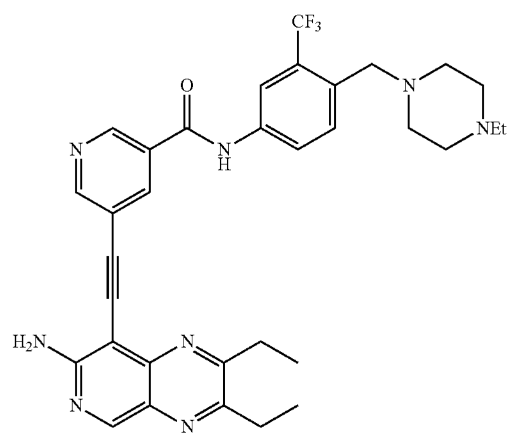
9
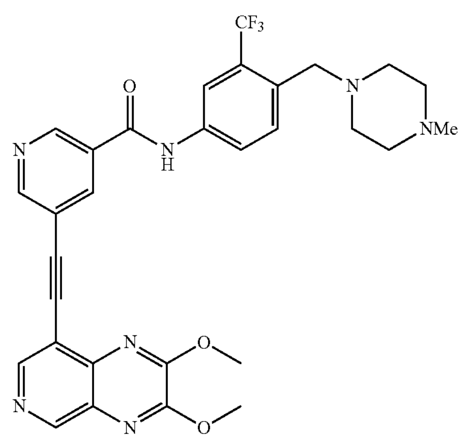

-continued
10
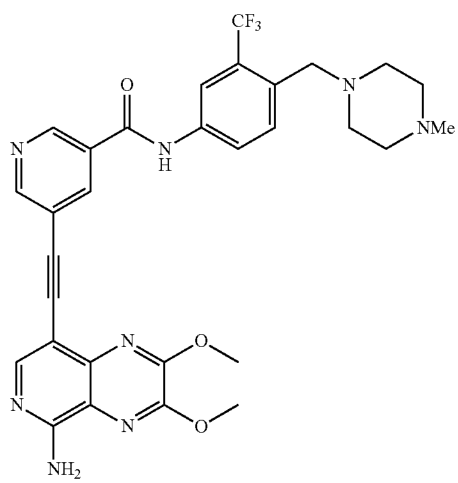
11
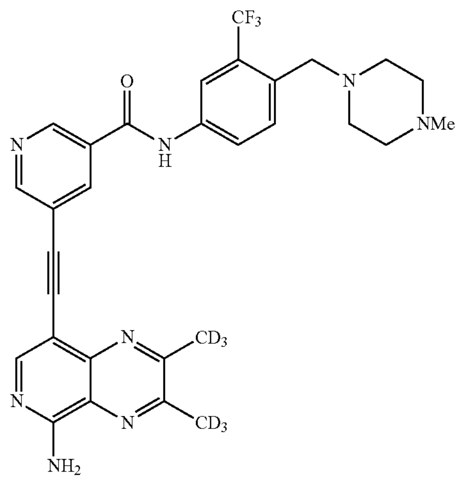
12
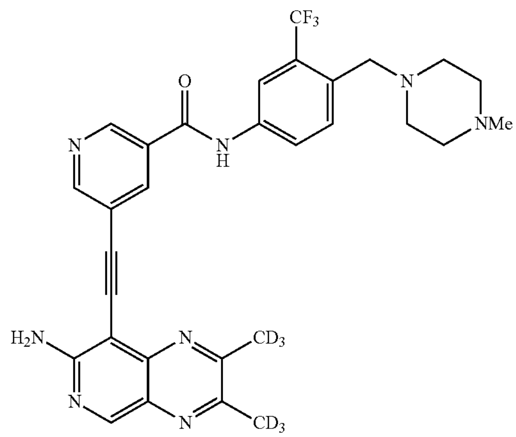
-continued
13
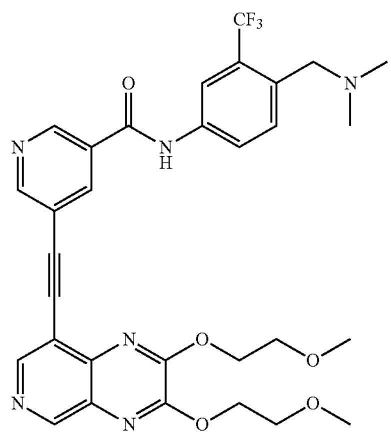
14
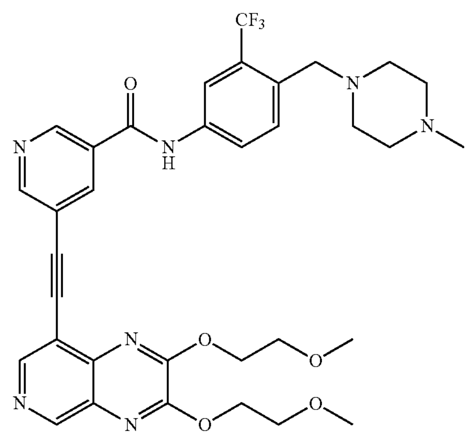
15
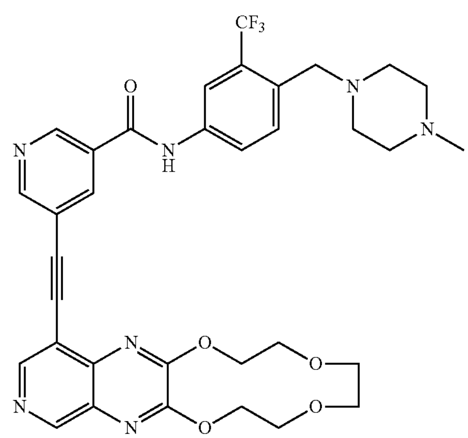

-continued
16
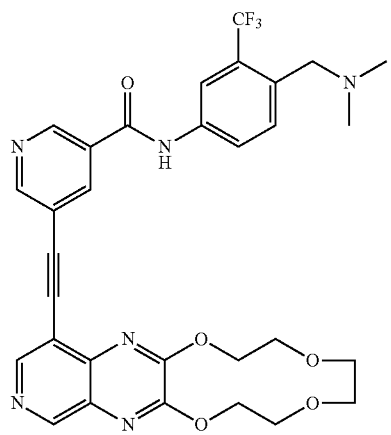
17
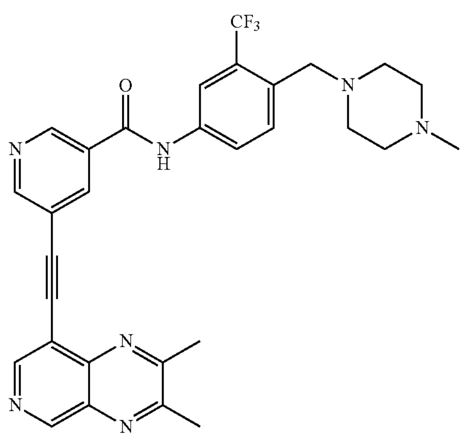
18
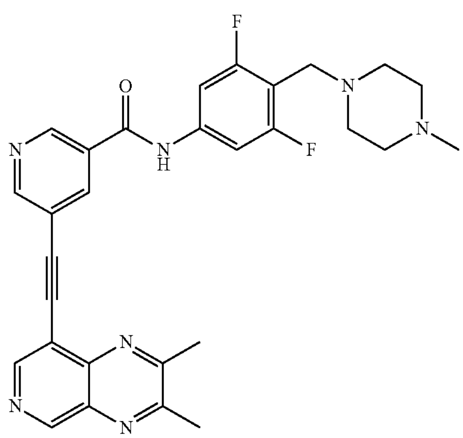
-continued
19
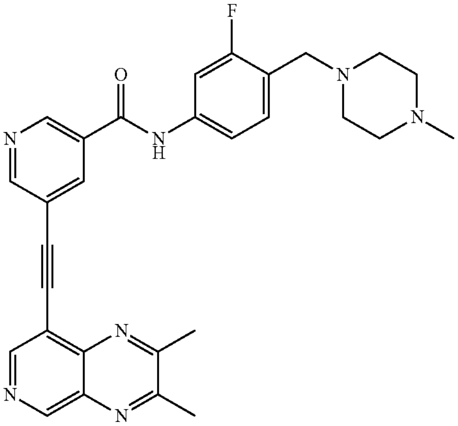
20
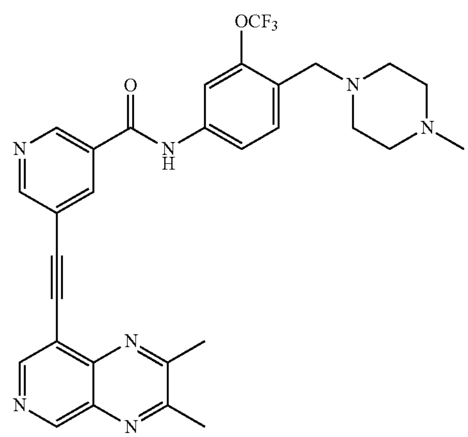
21
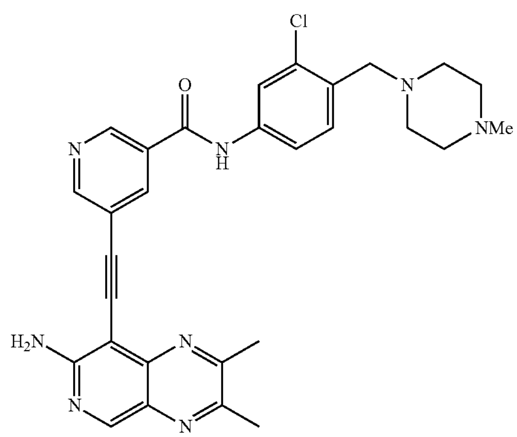

-continued
22
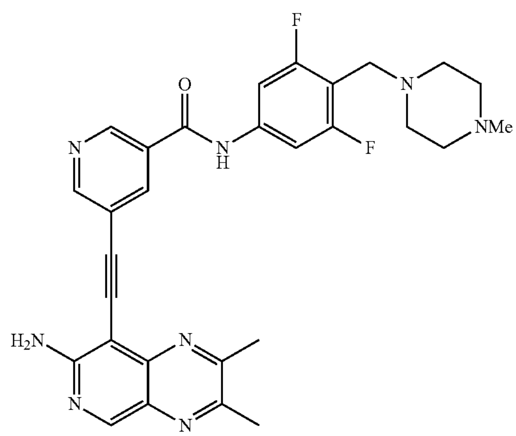
23
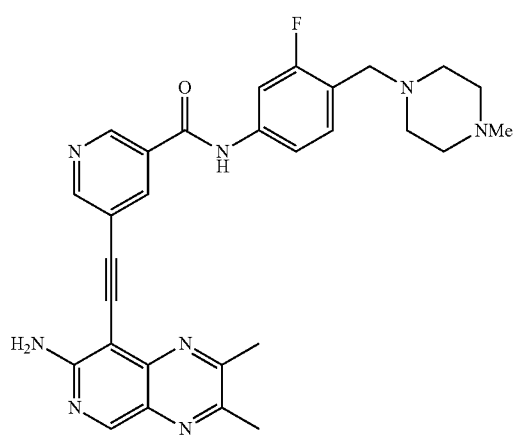
24
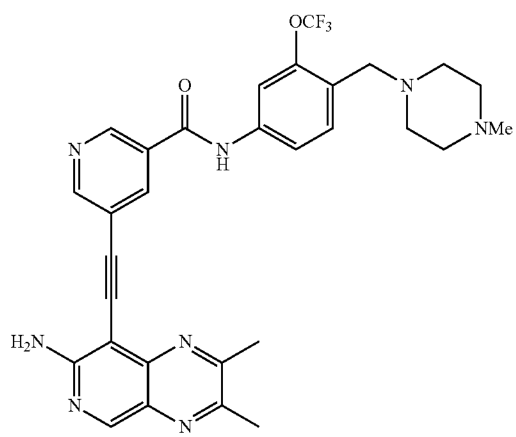
-continued
25
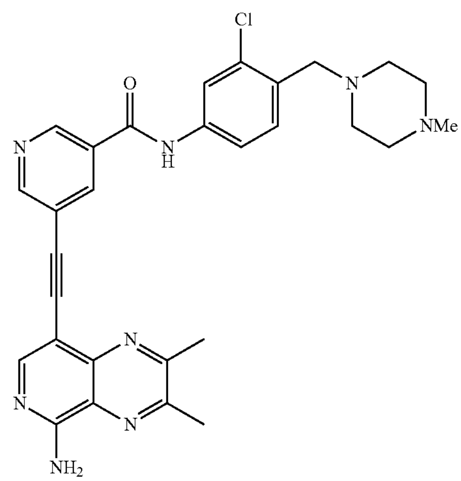
26
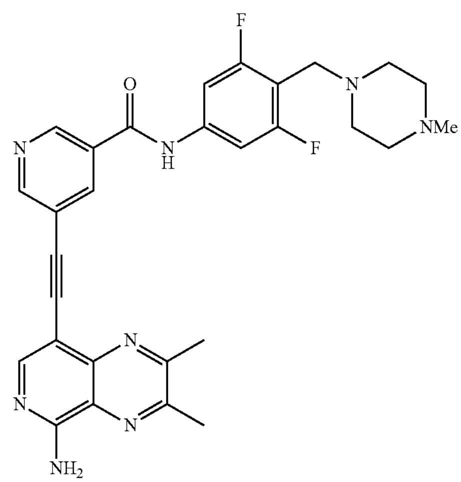
27
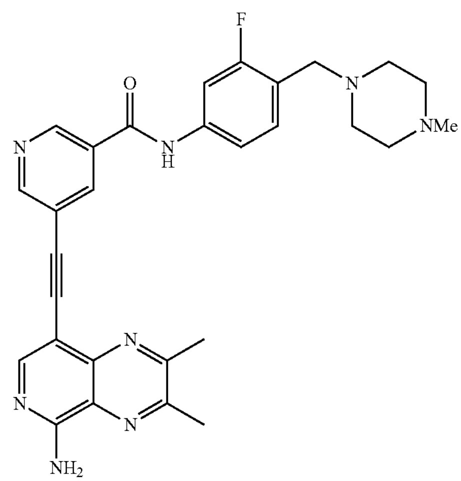

-continued
28
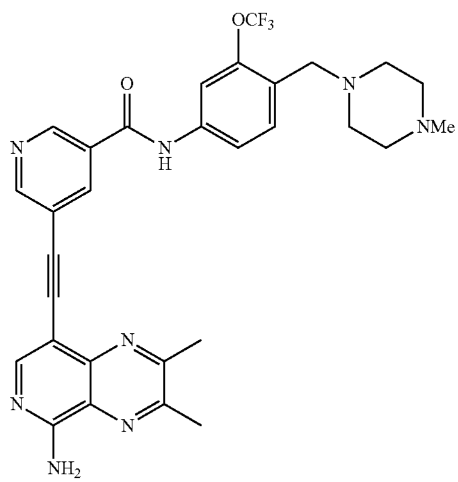
29
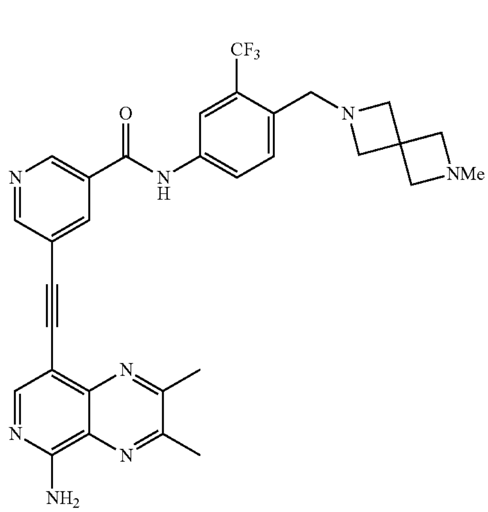
30
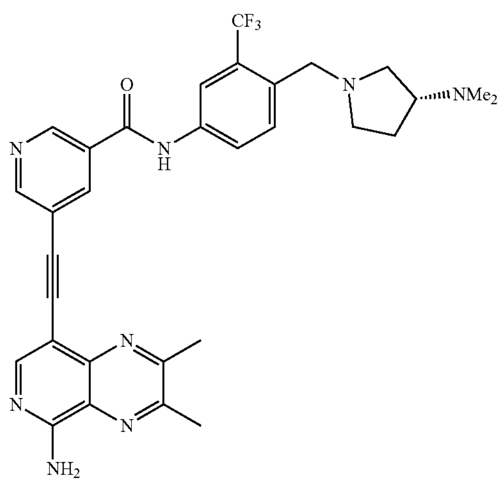
-continued
31
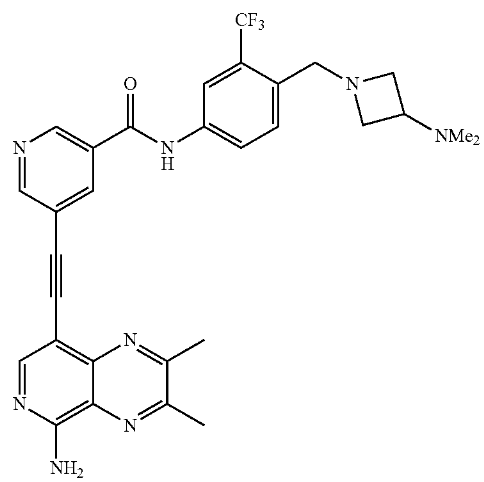
32
33
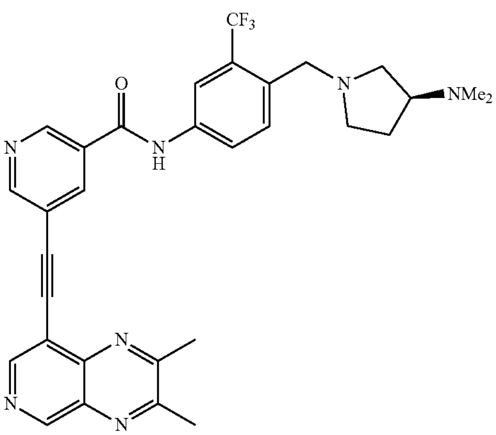

-continued
34
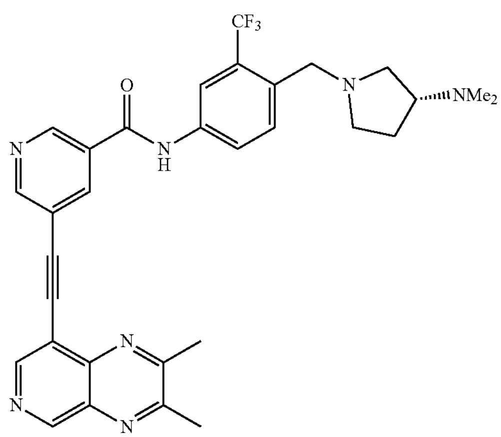
35
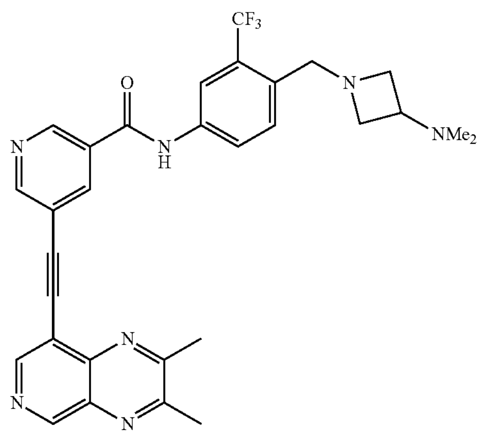
36
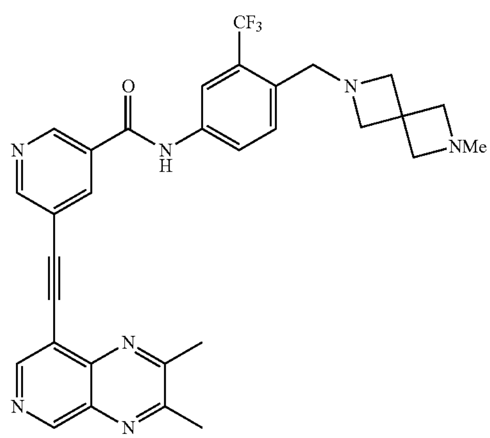
-continued
37
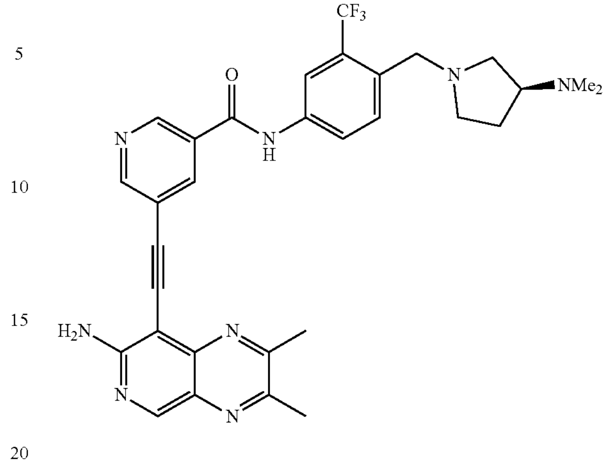
38
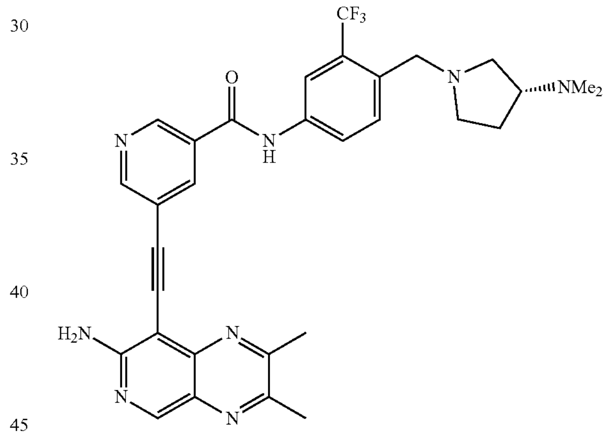
39
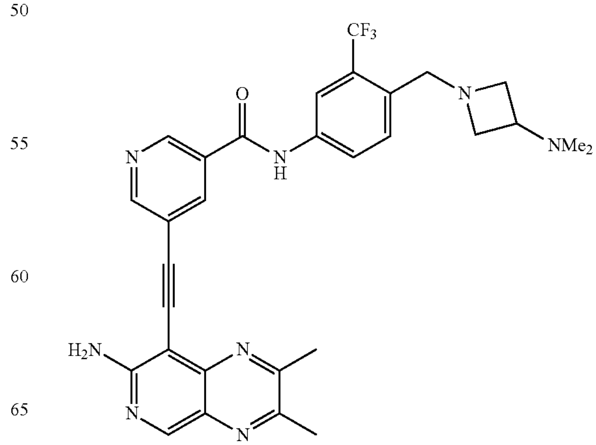

-continued
40
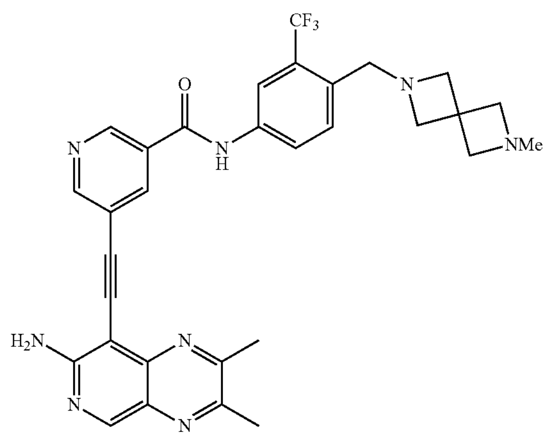
41
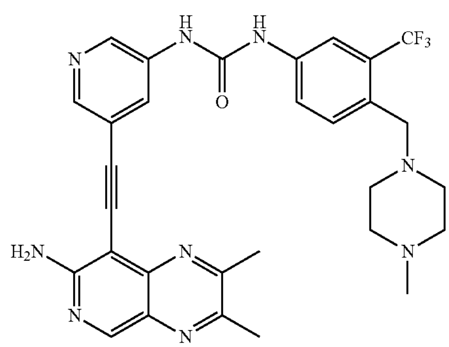
42
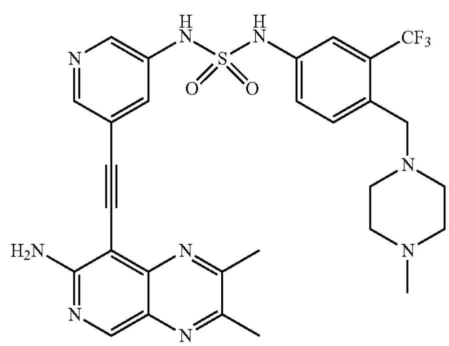
43
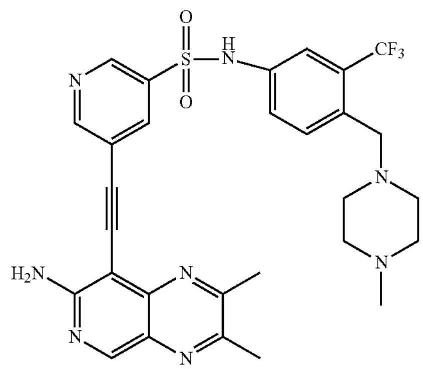
-continued
44
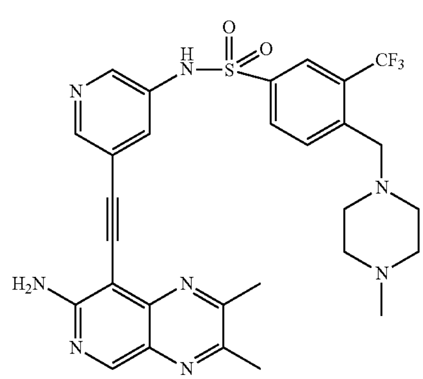
HSND65
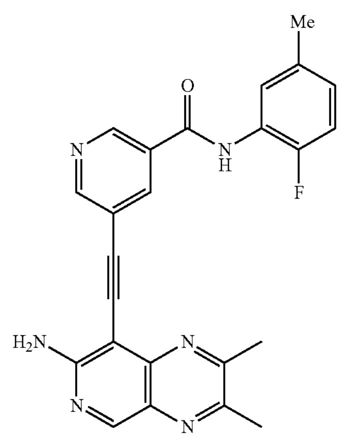
HSND66
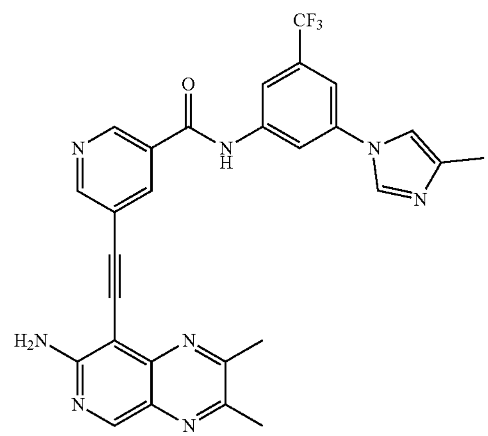

-continued
HSND67
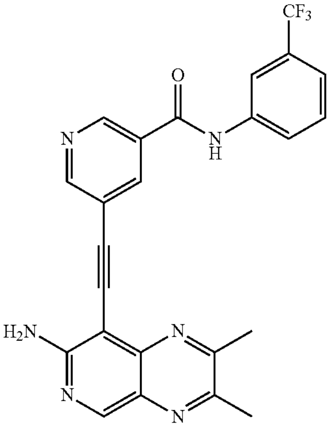
HSND68
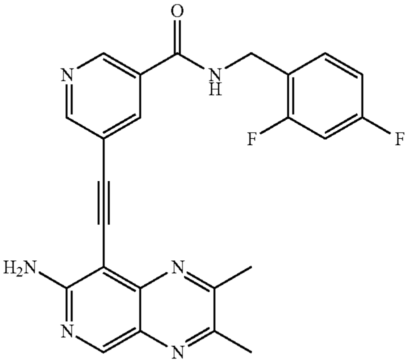
HSND69
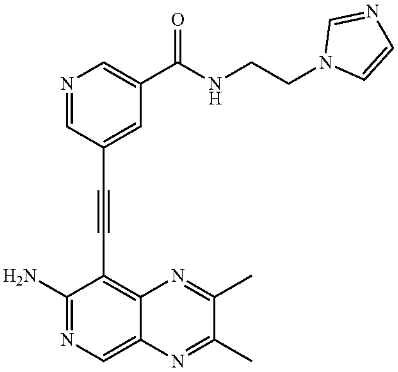
HSND70
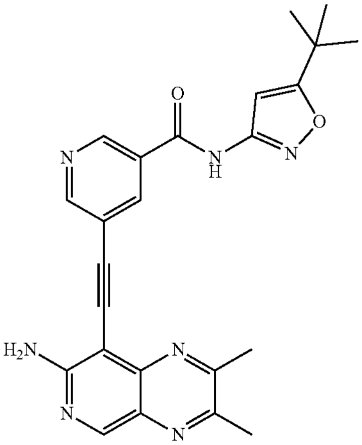
-continued
HSND72
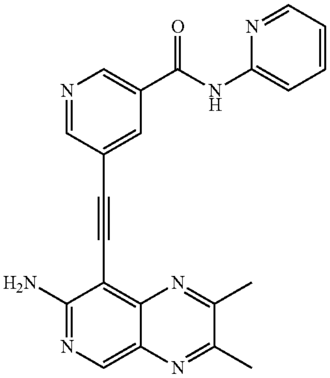
HSND73
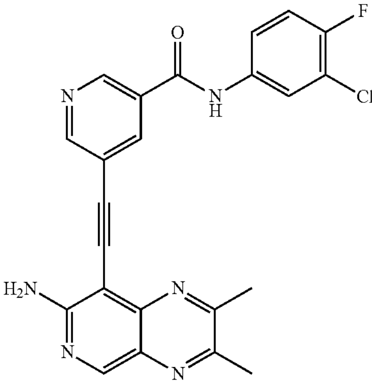
HSND67b
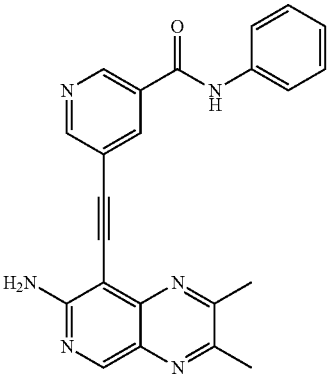
HSND67c
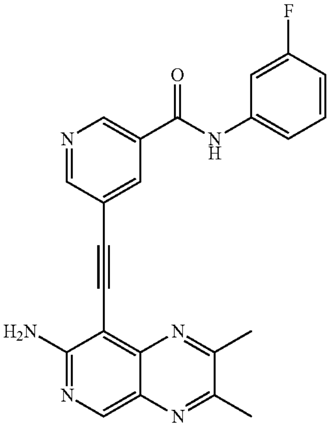

-continued
HSND67d
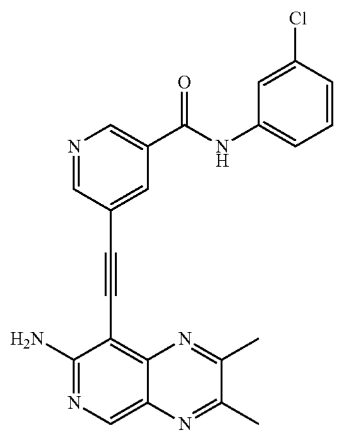
HSND67e
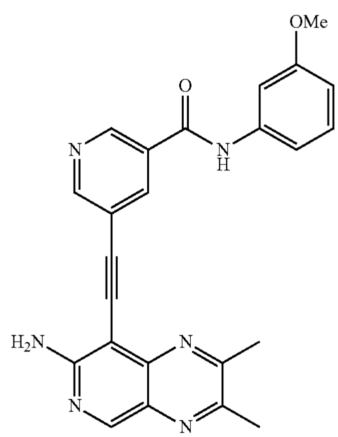
HSND67f
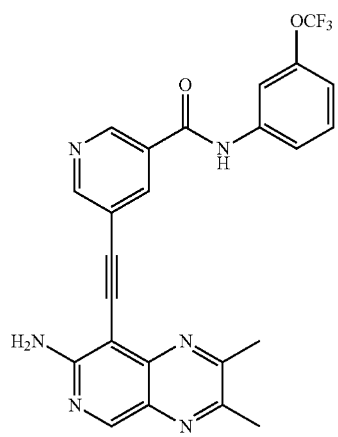
-continued
HSND67g
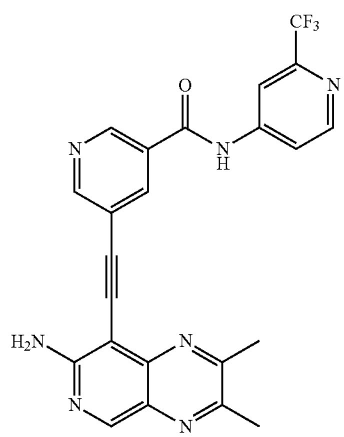
HSND67h
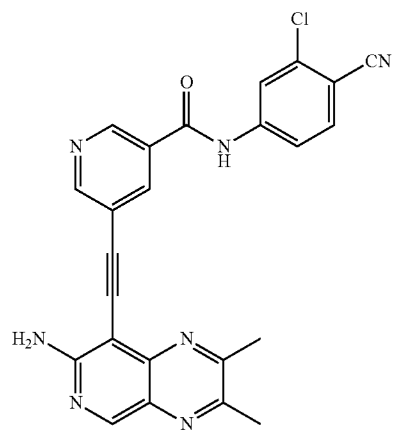
HSND67i
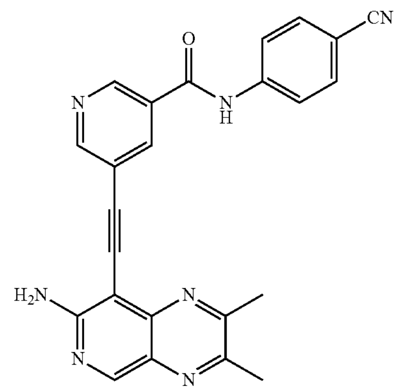

HSND67j
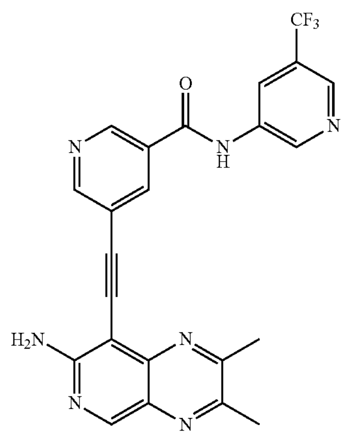
HSND67k
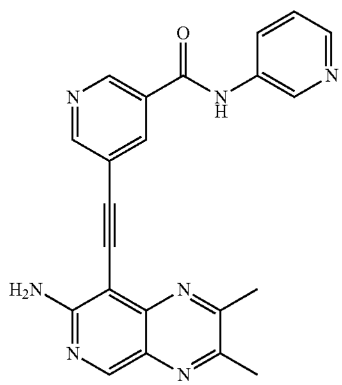
45
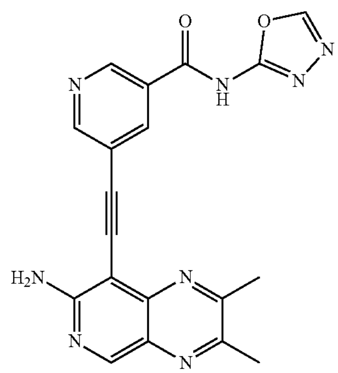
46
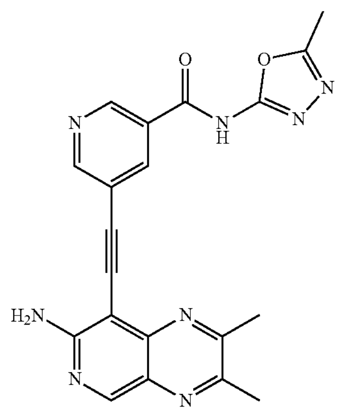
47
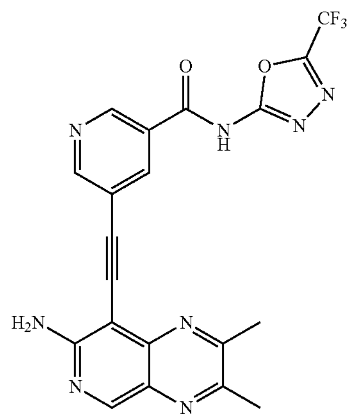
48
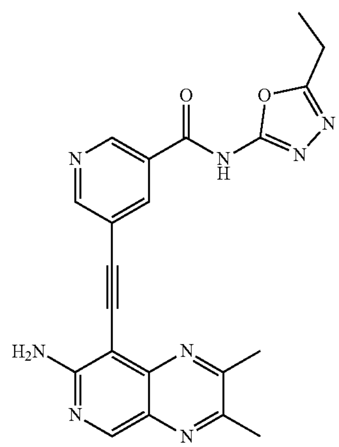
49
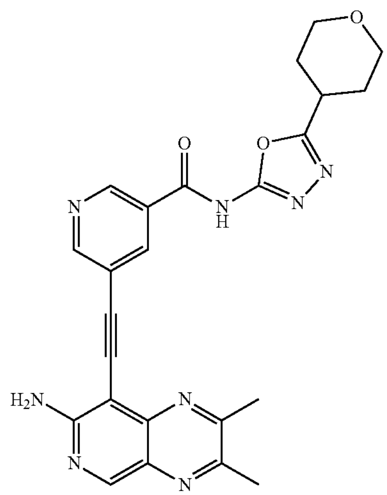

-continued
50
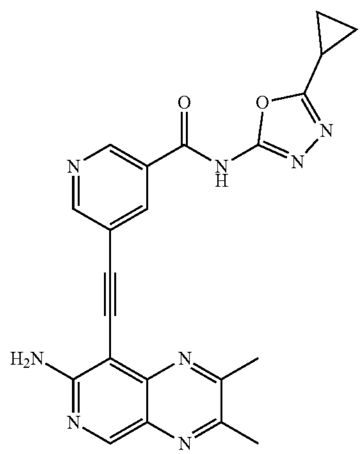
51
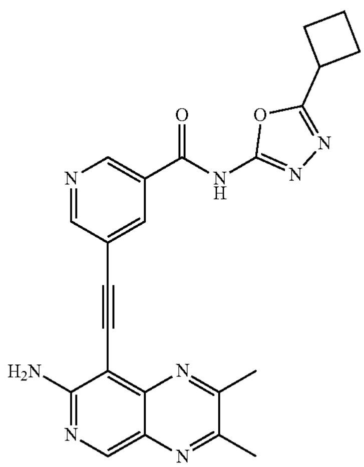
52
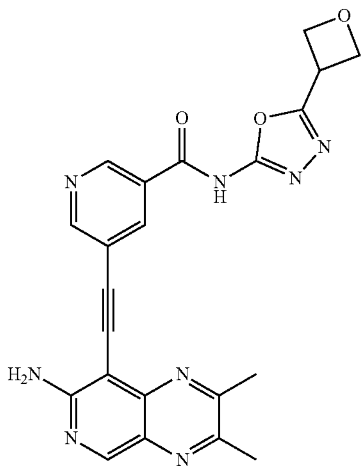
-continued
53
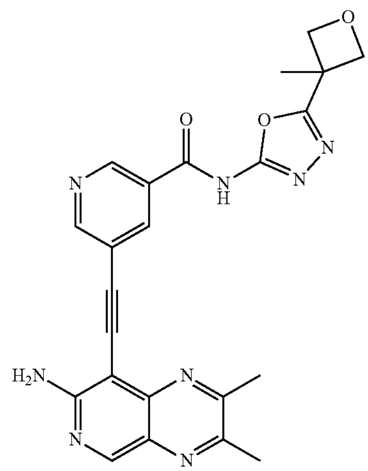
54
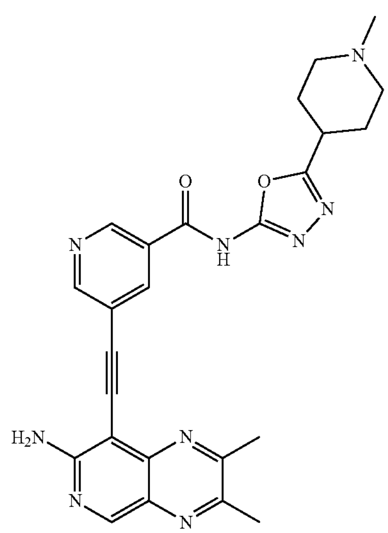
55
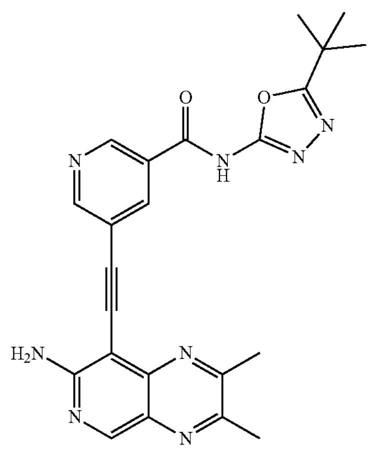

-continued
56
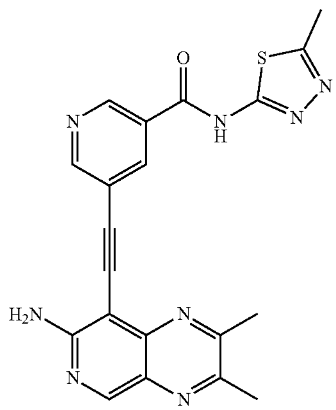
57
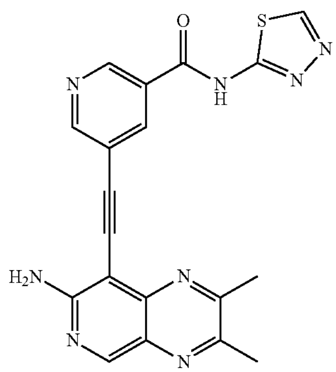
58
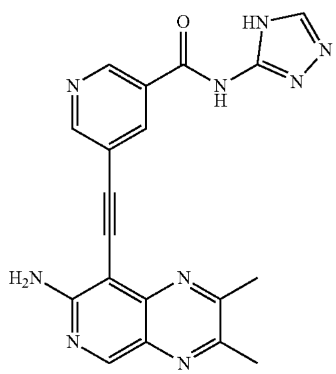
59
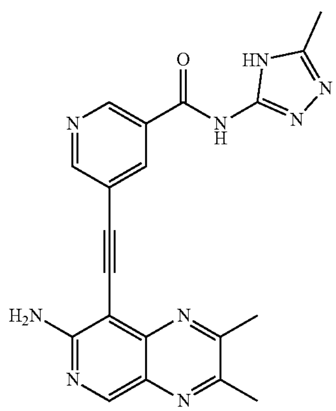
-continued
60
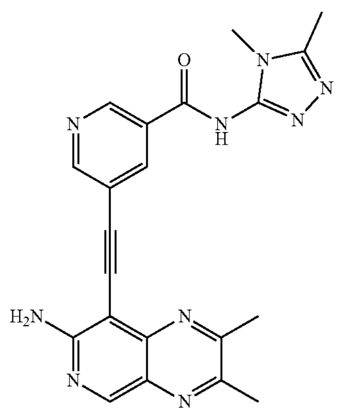
61
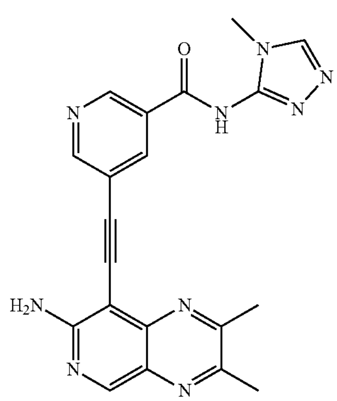
62
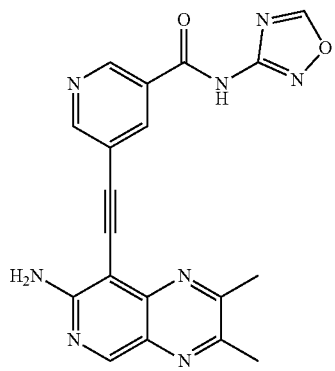
63
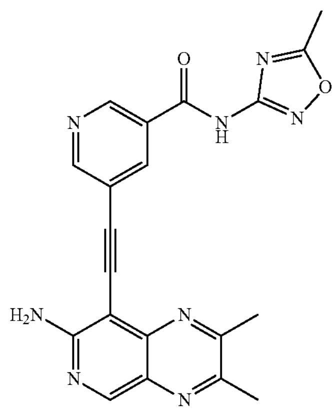

64
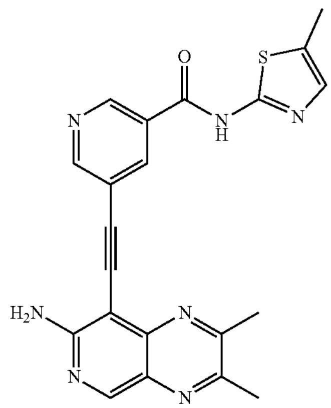
65
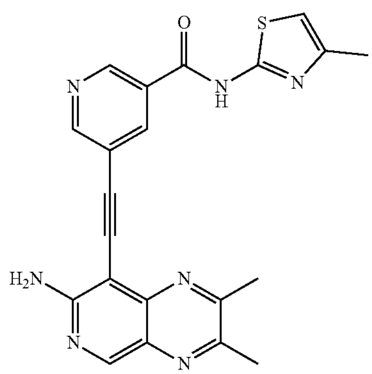
66
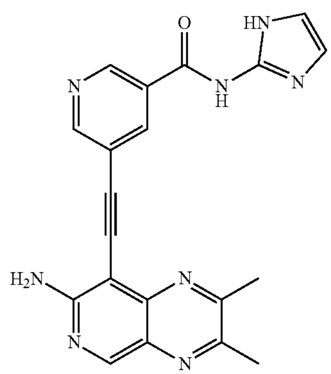
67
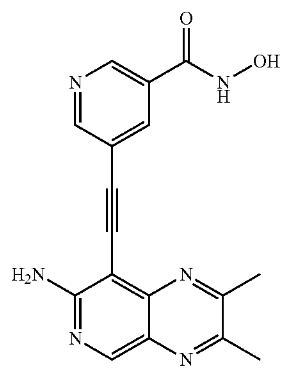
68
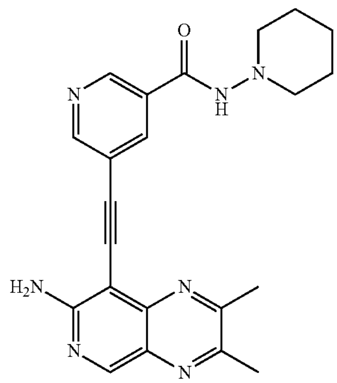
69
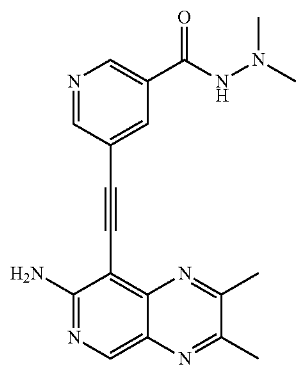
70
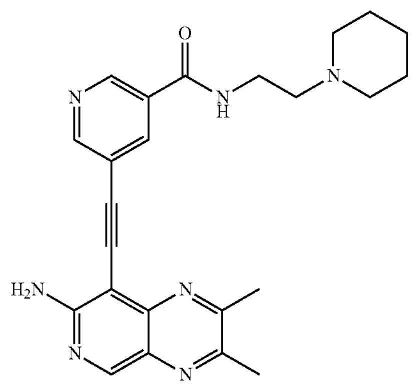
71
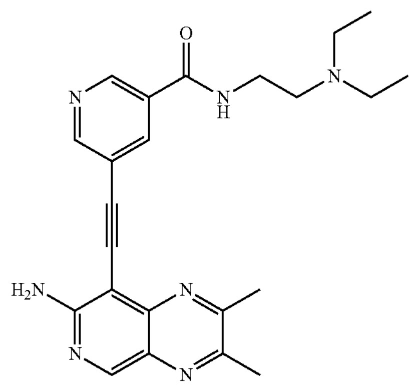

-continued
72
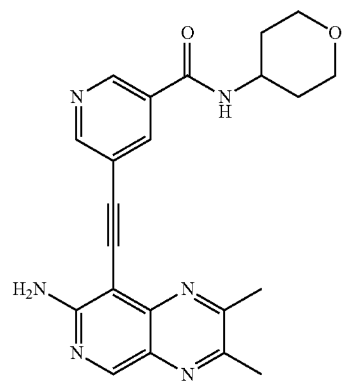
73
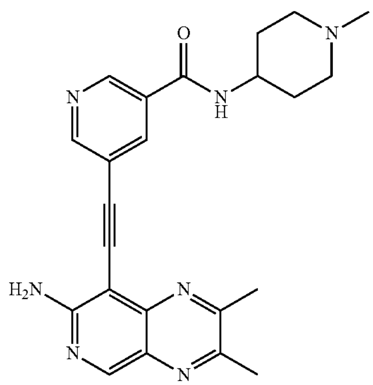
74
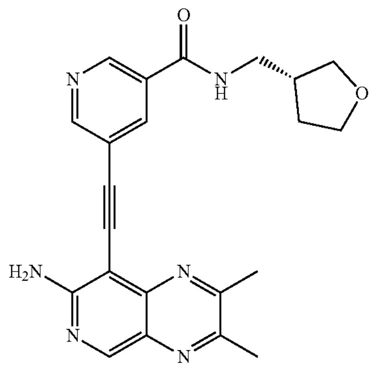
75
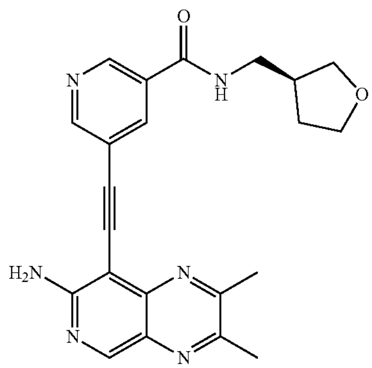
-continued
76
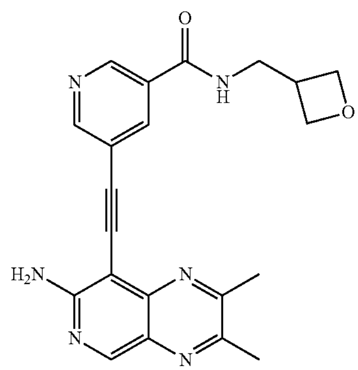
77
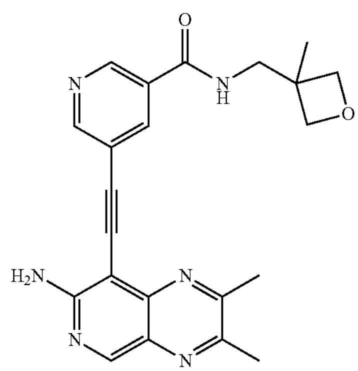
78
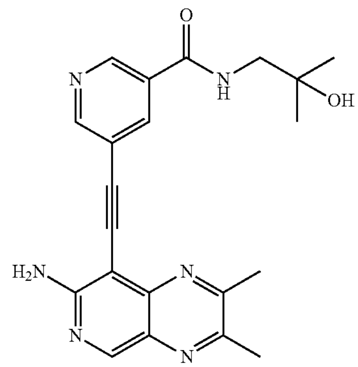
79
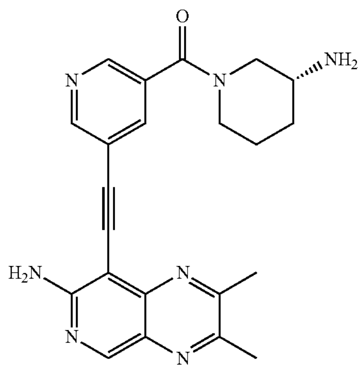

-continued
80
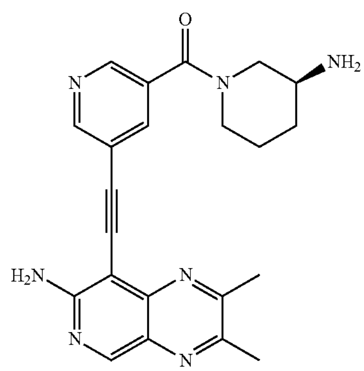
81
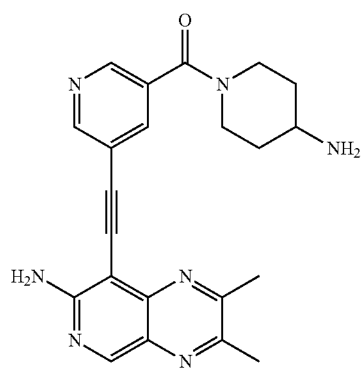
82
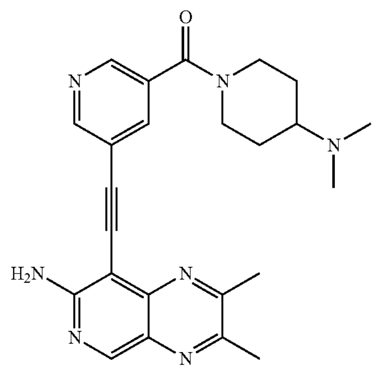
83
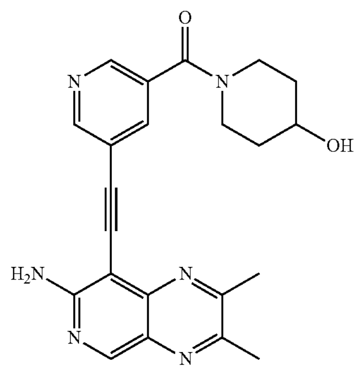
-continued
84
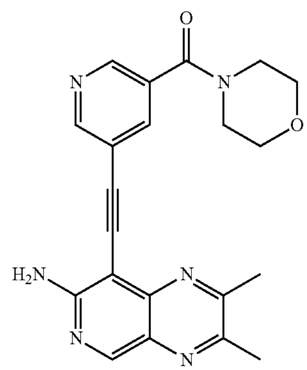
85
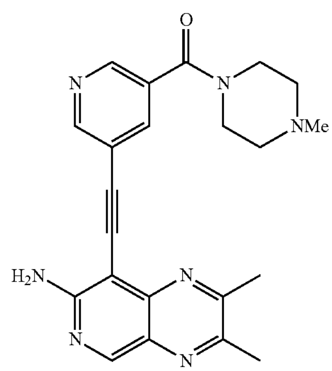
86
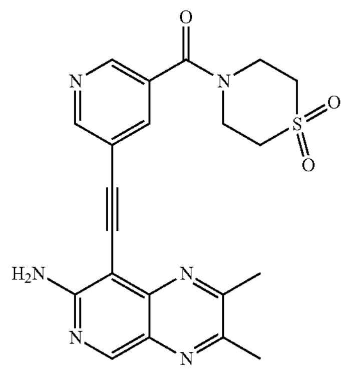
87
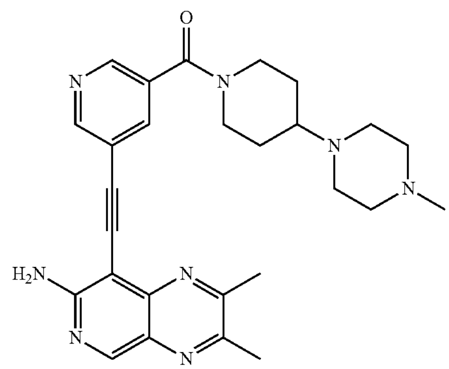

-continued
88
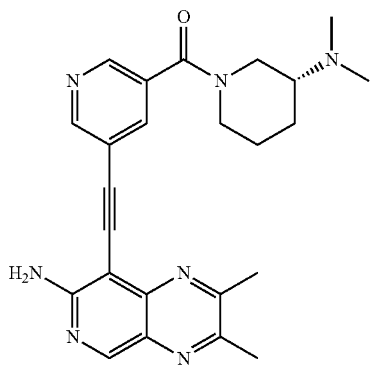
89
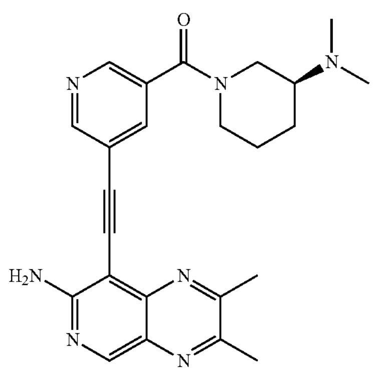
90
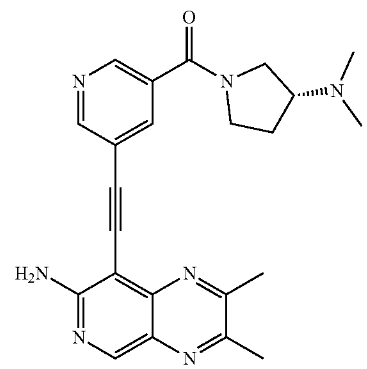
91
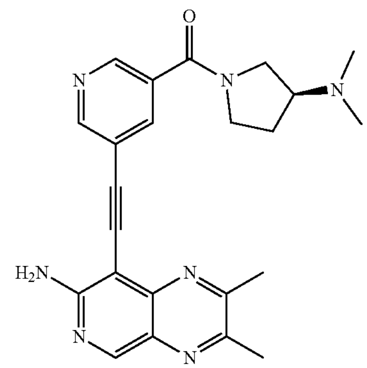
-continued
92
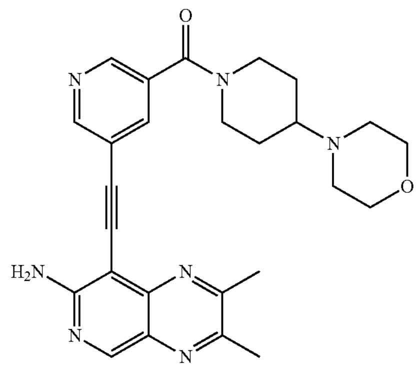
93
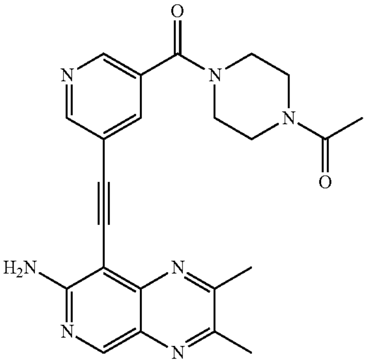
94
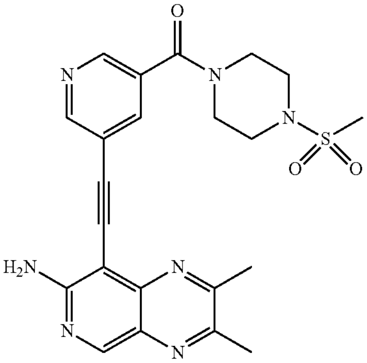
95
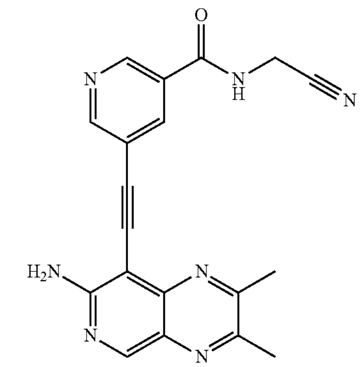

-continued
96
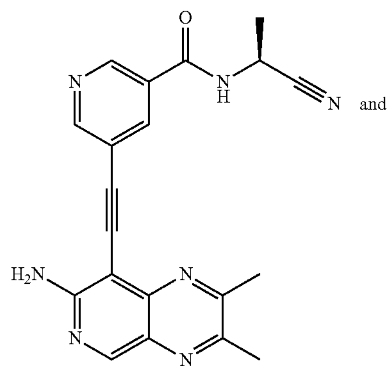
and
97
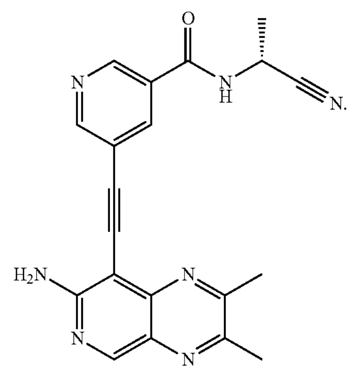
.
* * * * *